(12) United States Patent
Farr et al.

(10) Patent No.: US 8,597,299 B2
(45) Date of Patent: Dec. 3, 2013

(54) INSTRUMENTATION AND METHOD FOR PROVIDING SURGICAL ACCESS TO A SPINE

(75) Inventors: Morteza Farr, Santa Cruz, CA (US); Joshua Butters, Chandler, AZ (US); T. Wade Fallin, Hyde Park, UT (US)

(73) Assignee: Innovative Spine, LLC, Colvis, CA (US)

( * ) Notice: Subject to any disclaimer, the term of this patent is extended or adjusted under 35 U.S.C. 154(b) by 1285 days.

(21) Appl. No.: 11/934,636

(22) Filed: Nov. 2, 2007

(65) Prior Publication Data
US 2008/0255563 A1    Oct. 16, 2008

Related U.S. Application Data

(60) Provisional application No. 60/856,682, filed on Nov. 3, 2006.

(51) Int. Cl.
*A61B 17/70*    (2006.01)

(52) U.S. Cl.
USPC ............................................. 606/86 A

(58) Field of Classification Search
USPC ........................................ 606/99, 86 A, 914
See application file for complete search history.

(56) References Cited

U.S. PATENT DOCUMENTS

| | | |
|---|---|---|
| 3,090,386 A | 5/1963 | Curtis |
| 3,556,103 A | 1/1971 | Calhoun et al. |
| 3,570,498 A | 3/1971 | Weighton |
| 3,608,539 A | 9/1971 | Miller |
| 3,941,127 A | 3/1976 | Froning |
| 3,946,740 A | 3/1976 | Basset |
| 3,948,274 A | 4/1976 | Zeldman et al. |
| 3,964,480 A | 6/1976 | Froning |
| 4,265,231 A | 5/1981 | Scheller, Jr. et al. |
| 4,312,337 A | 1/1982 | Donohue |
| 4,335,715 A | 6/1982 | Kirkley |
| 4,511,356 A | 4/1985 | Froning et al. |
| 4,541,423 A | 9/1985 | Barber |

(Continued)

FOREIGN PATENT DOCUMENTS

WO    WO 2005/032358 A2    4/2005

OTHER PUBLICATIONS

Mazor Surgical Technologies, http://www.mazorst.com/SpineAssist-product.asp 2008 Website.

(Continued)

*Primary Examiner* — Sameh Boles
(74) *Attorney, Agent, or Firm* — GSS Law Group

(57) ABSTRACT

A system for accessing a spine from a curved postero-lateral approach may include a curved cannula positioned along a curved path from an opening in the skin to a location proximate the spine. A targeting post may be inserted adjacent the spine to determine the location. A peritoneal retractor and a guide member may be first inserted to establish the path between the tissues and fascia, and one or more intermediate cannulas may be temporarily inserted over the guide member to dilate the tissues prior to insertion of the main cannula. An interbody device may be implanted in an intervertebral space through the cannula. An endoscope may be inserted through the targeting post or the cannula. The system may include instruments with shafts which are flexible or are curved to match the curve of the curved cannula, including a rongeur, curette, rasp, distractor, trial implant, probe, tamp, and implant inserter.

9 Claims, 29 Drawing Sheets

(56) References Cited

U.S. PATENT DOCUMENTS

| | | |
|---|---|---|
| 4,545,374 A | 10/1985 | Jacobson |
| 4,573,448 A | 3/1986 | Kambin |
| 4,598,705 A | 7/1986 | Lichtenberger |
| 4,686,972 A | 8/1987 | Kurland |
| 4,722,331 A | 2/1988 | Fox |
| 4,756,708 A | 7/1988 | Martin |
| 4,863,430 A | 9/1989 | Klyce et al. |
| 4,883,048 A | 11/1989 | Purnell et al. |
| 4,926,860 A | 5/1990 | Stice et al. |
| 4,957,495 A | 9/1990 | Kluger |
| 5,080,662 A | 1/1992 | Paul |
| 5,163,940 A | 11/1992 | Bourque |
| 5,242,444 A | 9/1993 | MacMillan |
| 5,285,795 A | 2/1994 | Ryan |
| 5,300,077 A | 4/1994 | Howell |
| 5,330,468 A | 7/1994 | Burkhart |
| 5,334,205 A | 8/1994 | Cain |
| 5,458,602 A | 10/1995 | Goble et al. |
| 5,601,562 A | 2/1997 | Wolf |
| 5,613,971 A | 3/1997 | Lower |
| 5,725,532 A | 3/1998 | Shoemaker |
| 5,741,261 A | 4/1998 | Moskovitz et al. |
| 5,891,147 A | 4/1999 | Moskovitz et al. |
| 6,042,582 A | 3/2000 | Ray |
| 6,080,155 A | 6/2000 | Michelson |
| 6,083,225 A | 7/2000 | Winslow |
| 6,224,603 B1 | 5/2001 | Marino |
| 6,226,548 B1 | 5/2001 | Foley et al. |
| 6,419,678 B1 | 7/2002 | Asfora |
| 6,443,988 B2 | 9/2002 | Felt et al. |
| 6,530,929 B1 | 3/2003 | Justis et al. |
| 6,547,795 B2 | 4/2003 | Schneiderman |
| 6,575,899 B1 | 6/2003 | Foley et al. |
| 6,592,559 B1 | 7/2003 | Pakter et al. |
| 6,604,003 B2 | 8/2003 | Fredricks et al. |
| 6,638,276 B2 | 10/2003 | Sharkey et al. |
| 6,669,698 B1 | 12/2003 | Tromanhauser et al. |
| 6,689,140 B2 | 2/2004 | Cohen |
| 6,733,496 B2 | 5/2004 | Sharkey et al. |
| 6,740,090 B1 | 5/2004 | Cragg et al. |
| 6,764,491 B2 | 7/2004 | Frey et al. |
| 6,790,210 B1 | 9/2004 | Cragg et al. |
| 6,796,983 B1 | 9/2004 | Zucherman et al. ............ 606/61 |
| 6,824,565 B2 | 11/2004 | Muhanna et al. |
| 6,830,570 B1 | 12/2004 | Frey et al. |
| 6,875,219 B2 | 4/2005 | Arramon et al. |
| 6,980,862 B2 | 12/2005 | Fredricks et al. |
| 7,008,422 B2 | 3/2006 | Foley et al. |
| 7,011,660 B2 | 3/2006 | Sherman et al. |
| RE39,133 E | 6/2006 | Clayton et al. |
| 7,060,068 B2 | 6/2006 | Tromanhauser et al. |
| 7,060,073 B2 | 6/2006 | Frey et al. |
| 7,074,226 B2 | 7/2006 | Roehm et al. |
| 2002/0013514 A1 | 1/2002 | Brau |
| 2002/0019637 A1 | 2/2002 | Frey et al. |
| 2002/0065541 A1 | 5/2002 | Fredricks et al. |
| 2002/0091387 A1 | 7/2002 | Hoogland |
| 2002/0156420 A1 | 10/2002 | Anderson et al. |
| 2002/0161368 A1 | 10/2002 | Foley et al. |
| 2002/0165550 A1 | 11/2002 | Frey et al. |
| 2003/0032929 A1 | 2/2003 | McGuckin |
| 2003/0120308 A1 | 6/2003 | Loubens |
| 2003/0191474 A1 | 10/2003 | Cragg et al. |
| 2003/0199871 A1 | 10/2003 | Foley et al. |
| 2003/0208202 A1 | 11/2003 | Falahee |
| 2004/0015215 A1 | 1/2004 | Fredricks et al. |
| 2004/0030346 A1 | 2/2004 | Frey et al. |
| 2004/0034351 A1 | 2/2004 | Sherman et al. |
| 2004/0038242 A1 | 2/2004 | Edmonds et al. |
| 2004/0092928 A1 | 5/2004 | Sasso |
| 2004/0106997 A1 | 6/2004 | Lieberson |
| 2004/0117020 A1 | 6/2004 | Frey et al. |
| 2004/0133168 A1 | 7/2004 | Salcudean et al. |
| 2004/0153005 A1 | 8/2004 | Krueger |
| 2004/0162559 A1 | 8/2004 | Arramon |
| 2004/0199168 A1 | 10/2004 | Bertagnoli et al. |
| 2004/0215190 A1 | 10/2004 | Nguyen et al. |
| 2004/0220577 A1 | 11/2004 | Cragg et al. |
| 2005/0021031 A1 | 1/2005 | Foley et al. |
| 2005/0137605 A1 | 6/2005 | Assell et al. |
| 2005/0137612 A1 | 6/2005 | Assell et al. |
| 2005/0149035 A1 | 7/2005 | Pimenta et al. |
| 2005/0171540 A1 | 8/2005 | Lim et al. |
| 2005/0177239 A1 | 8/2005 | Steinberg |
| 2005/0187543 A1 | 8/2005 | Underwood et al. |
| 2005/0209610 A1 | 9/2005 | Carrison |
| 2005/0261773 A1 | 11/2005 | Ferree |
| 2006/0009780 A1 | 1/2006 | Foley et al. |
| 2006/0036241 A1 | 2/2006 | Siegal |
| 2006/0036273 A1 | 2/2006 | Siegal |
| 2006/0052848 A1 | 3/2006 | Fredricks et al. |
| 2006/0064101 A1 | 3/2006 | Arramon |
| 2006/0084977 A1 | 4/2006 | Lieberman |
| 2006/0111714 A1 | 5/2006 | Foley |
| 2006/0129101 A1 | 6/2006 | McGuckin, Jr. et al. |
| 2006/0135915 A1 | 6/2006 | Tucker |
| 2006/0135916 A1 | 6/2006 | Tucker |
| 2006/0149278 A1 * | 7/2006 | Abdou ............................ 606/90 |
| 2006/0189986 A1 | 8/2006 | Sherman et al. |
| 2006/0195102 A1 | 8/2006 | Malandain |
| 2006/0200129 A1 | 9/2006 | Denti |
| 2006/0200135 A1 | 9/2006 | Sherman et al. |
| 2006/0217806 A1 | 9/2006 | Peterman et al. |
| 2006/0217807 A1 | 9/2006 | Peterman et al. |
| 2006/0229614 A1 | 10/2006 | Foley et al. |
| 2006/0264968 A1 | 11/2006 | Frey et al. |

OTHER PUBLICATIONS

International Search Report and Written Opinion From Corresponding PCT Application No. PCT/US2007/083625, Aug. 6, 2008 (8 pgs).

* cited by examiner

US 8,597,299 B2

INSTRUMENTATION AND METHOD FOR PROVIDING SURGICAL ACCESS TO A SPINE

CROSS-REFERENCE TO RELATED APPLICATIONS

This application claims the benefit of reference: U.S. Provisional Patent Application No. 60/856,682, filed Nov. 3, 2006, which is entitled METHOD AND APPARATUS FOR SPINAL SURGERY.

BACKGROUND OF THE INVENTION

1. The Field of the Invention

The invention relates to orthopaedics, and more particularly, to systems and methods for providing access to the spine to facilitate various implantation procedures.

2. The Relevant Technology

Many spinal orthopaedic procedures including discectomy, implantation of motion preservation devices, total disc replacement, and implantation of interbody devices require unimpeded access to a targeted portion of the spinal column. A lateral interbody fusion approach requires the patient to be turned mid-process to complete the disc and interbody device procedures and posterior hardware stabilization procedures. An anterior approach requires the presence of a vascular surgeon or highly experienced general surgeon, due to the risk of injury to vascular anatomy. Accordingly, there is a need in the art for systems and methods that facilitate access to the spine, thereby simplifying surgical procedures and expediting patient recovery.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to systems and methods for accessing intervertebral space and inserting spine implants between vertebral bodies. Those of skill in the art will recognize that the following description is merely illustrative of the principles of the invention, which may be applied in various ways to provide many different alternative embodiments. This description is made for the purpose of illustrating the general principles of this invention and is not meant to limit the inventive concepts in the appended claims.

The present invention provides access to the spine through the use of a postero-lateral approach. A minimally invasive dilation and/or access device employing such an approach would have significant advantages in spinal orthopaedic procedures over the lateral and anterior approaches. These advantages may include avoiding the need to turn the patient during surgery, less muscle retraction, less blood loss, less operating room time, minimized damage to the vascular system, organs, nerves and muscles, faster recovery, and an improved overall outcome for the patient.

Figure 1:
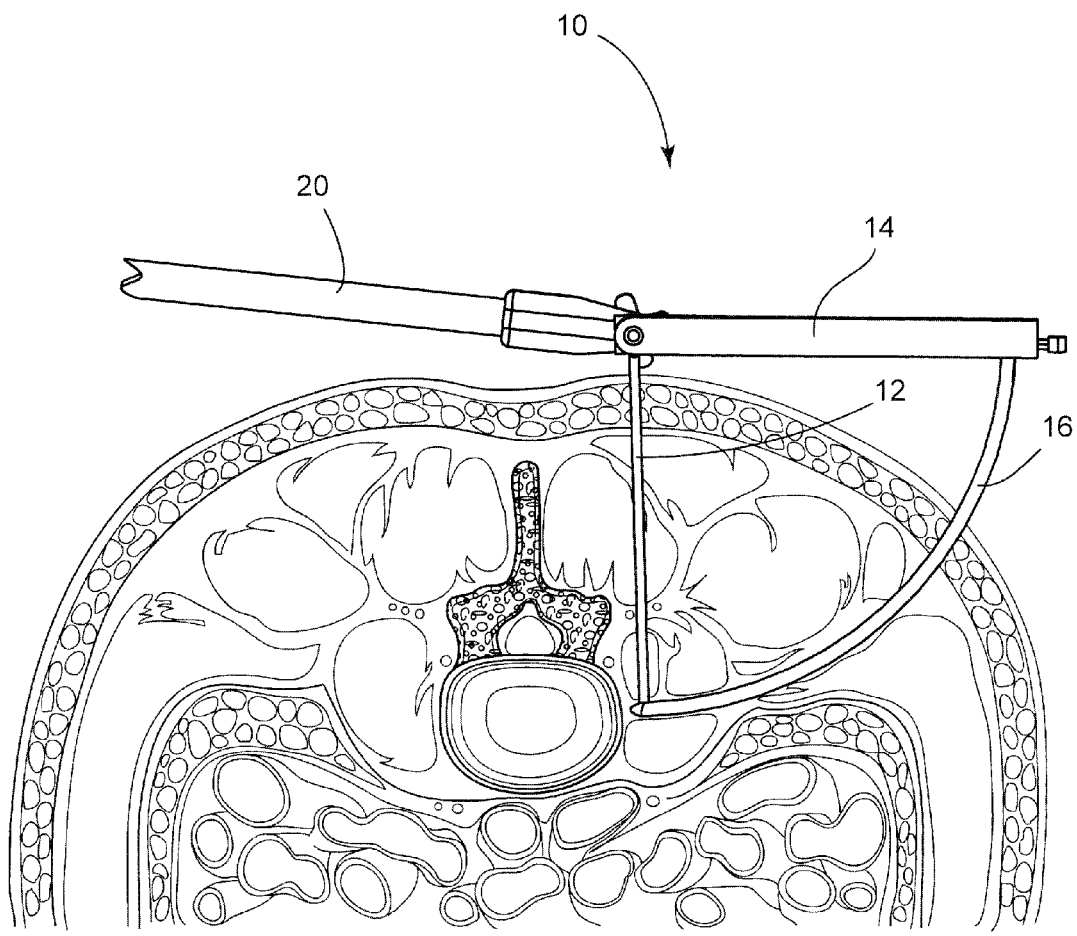
FIG. 1 is a cephalad view of a cross-section of a portion of a patient with an arcuate cannula assembly deployed adjacent a portion of the spine.

Referring to FIG. 1, one embodiment of an arcuate cannula assembly 10 is shown. The assembly 10 comprises a targeting post 12, a guide arm 14, and a curved penetrating guide member 16. An instrument support arm 20 holds the assembly and connects to an operating table (not shown). The assembly 10 may further comprise a series of graduated curved cannulas (net shown in FIG. 11), which are introduced sequentially over the guide member 16 to create access to a targeted portion of a spine. Use of the cannula assembly 10 creates an access portal to the intervertebral disc space or any element of the anterior spinal column through an arcuate path, from a postero-lateral approach. The access portal is an unimpeded passage through which surgical instruments, implants and other materials may be passed to complete a variety of intervertebral procedures. This arcuate postero-lateral approach may be advantageous in performing a number of procedures, including but not limited to: implantation of motion preservation devices, total disk replacement, implantation of interbody devices, discectomy, lateral plating with or without dynamic elements, vertebra fixation or graft compression using plates or staples, foraminotomy, decompression, annulotomy, nucleotomy, annulus or nucleus repair, vertebral body biopsy, vertebroplasty, height restoration of a collapsed vertebral body (vertebral body augmentation), implantation of a fusion cage with stabilization features, implantation of a fusion cage with teeth to hold endplates together, or implantation of a curved or straight staple across the disc space to provide compression on the cage and stabilization of the cage.

Figure 2:
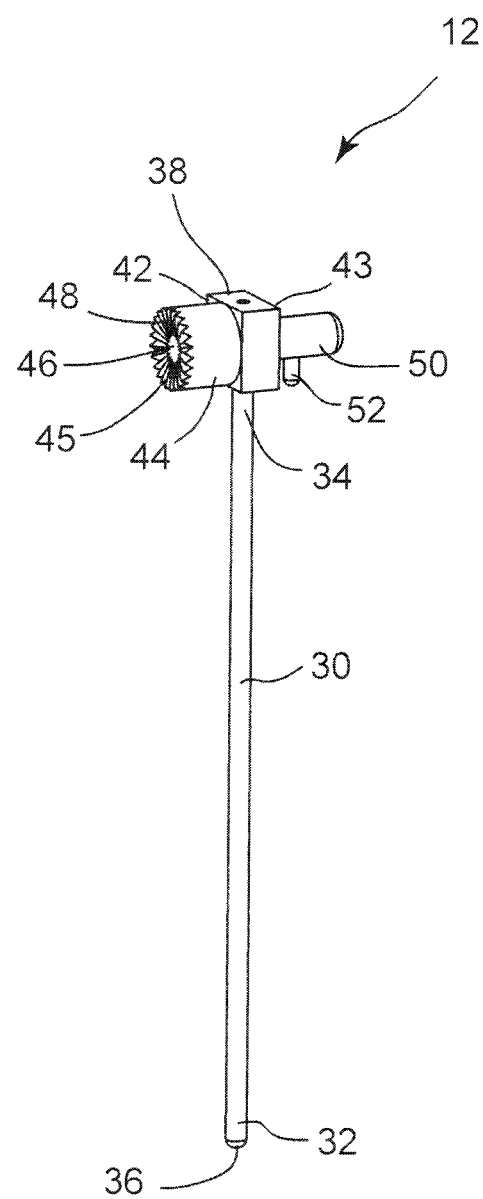
FIG. 2 is a perspective view of a targeting post of the arcuate cannula assembly of FIG. 1.

Referring to FIG. 2, a perspective view of the targeting post 12 is shown. The targeting post 12 comprises an elongate shaft 30 with a distal end 32 and a proximal end 34. A rounded tip 36 is at the terminus of the distal end 32. The proximal end 34 adjoins a rectangular connector block 38 which has a first side 42 and a second side 43. Adjoining the connector block 38 on the first side 42 is a support arm attachment post 44. The attachment post 44 has a receiving slot 46 which extends transversely into the attachment post through an interface surface 45. In the preferred embodiment the receiving slot 46 includes an internally threaded surface. A radial spline 48 encircles the receiving slot 46 on the interface surface 45. Adjoining the connector block 38 on the second side 43 is a rotation post 50. Extending distally from the rotation post 50 is an optional stop feature 52. An alternative embodiment may include a targeting post with a polyaxial joint, enabling the support arm 20 and/or guide arm 14 to be oriented at an angle relative to the targeting post.

Figure 3:
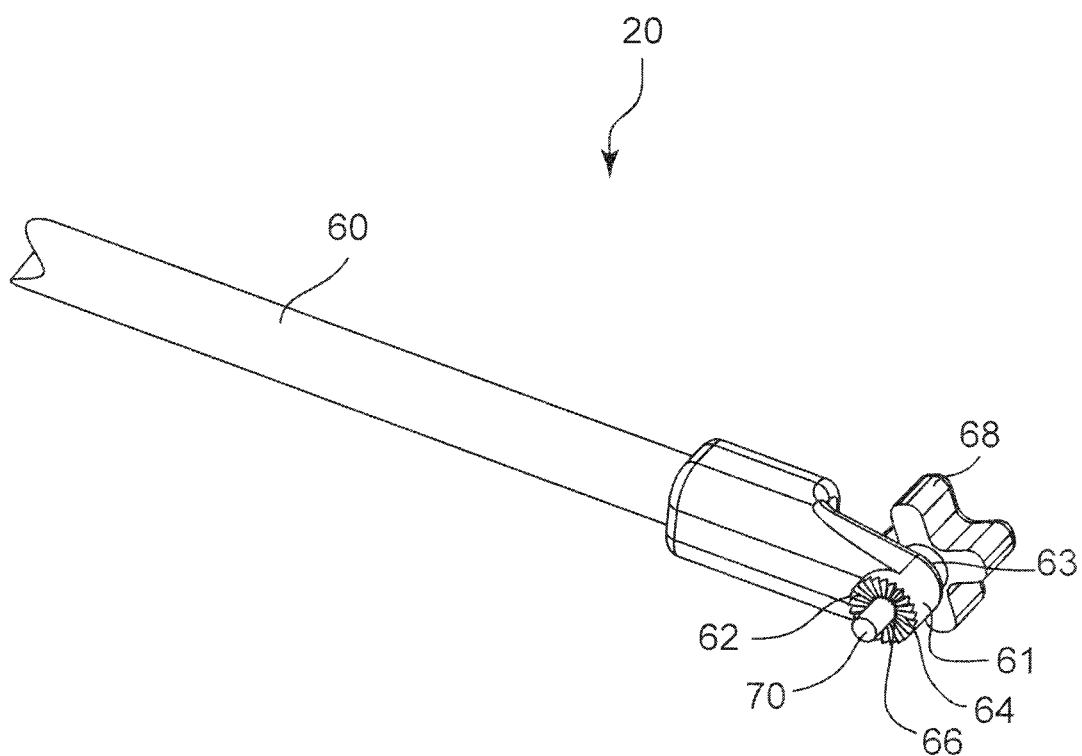
FIG. 3 is a perspective view of a portion of an instrument support arm.

Referring to FIG. 3, a perspective view of a support arm 20 is shown. The support arm 20 comprises a shaft 60 which attaches to the operating table via various linkages, pivots, or connections to allow multiple degrees of freedom to accommodate the positioning of the instrument to be held. A wide variety of differently-configured instrument support arms are well known in the art and the assembly 10 may be compatible with the instrument support arm of choice for the surgeon.

A distal end 61 of the shaft 60 has a first side 62 and a second side 63. Extending transversely through the distal end 61 from the first side 62 to the second side 63 is a screw channel 66. On the first side 62, an interface surface 65 has a radial spline 64 which encircles the opening of the screw channel 66. The radial spline 64 is configured to mate with the radial spline 48 on the targeting post 12 when the post is connected to the support arm 20. Extending through the channel 66 is a thumb screw 68, and a shaft 70 protrudes from the channel 66 on the second side 63. In the preferred embodiment, shaft 70 includes an externally threaded surface configured to interface with the threaded receiving slot 46 on the targeting post 12.

Figure 4:
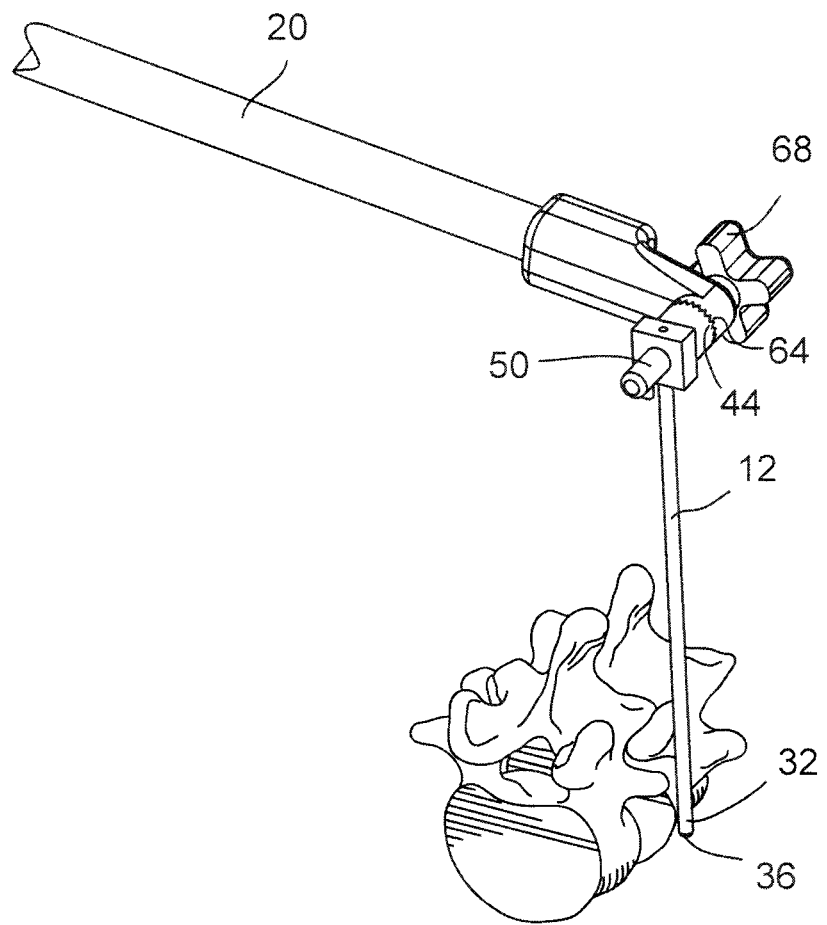
FIG. 4 is a perspective view of the instrument support arm of FIG. 3 supporting the targeting post of FIG. 2 adjacent a portion of a spine.

Referring to FIG. 4, the targeting post 12 is introduced into the patient from a postero-lateral approach through a small incision on the patient's back posterior to the targeted spine segment. The distal end 32 of the targeting post 12 is advanced antero-medially through the patient just lateral to the targeted intervertebral disc until the tip 36 reaches a desired reference location at the anterior lateral half or one third of the disc. The blunt shape of the tip 36 gently pushes tissues aside as the post 12 is advanced in. The post 12 may also be wired as an electrode during insertion, allowing for nerve monitoring or electromyography (EMG) to avoid nerves as the post 12 advances through the tissues. Of special concern is avoidance of the nerve roots exiting the spinal column as the psoas muscle adjacent to the spine is penetrated by the post 12. The targeting post 12 is inserted so that it is coplanar with the superior endplate of the inferior vertebral body for the intervertebral level to be treated. Preferably, the post 12 is aligned parallel with the sagittal plane of the patient, but other orientations are possible if necessary to avoid nerves or other obstacles. The targeting post 12 may be available in a variety of lengths to accommodate patients of differing proportions, and to reach specific reference locations.

When the distal end 32 of the targeting post 12 has reached the reference location, the proximal end 30 is attached to the support arm 20 via the thumb screw 68. The protruding screw shaft 70 is threaded into the receiving slot 46. As the thumb screw 68 is threaded in, the radial splines 44, 64 mesh, locking the targeting post 12 to the support arm 20. Once attachment is made between the targeting post 12 and the support arm 20, the various degrees of freedom of the support arm 20 are locked down to provide sufficiently rigid instrument stabilization. In position adjacent to the spine, the targeting post 12 acts as a stabilizing and reference guide for subsequent cannulas, instruments and implants. The targeting post 12 may optionally be affixed to the patient to provide additional stability.

Figure 5:
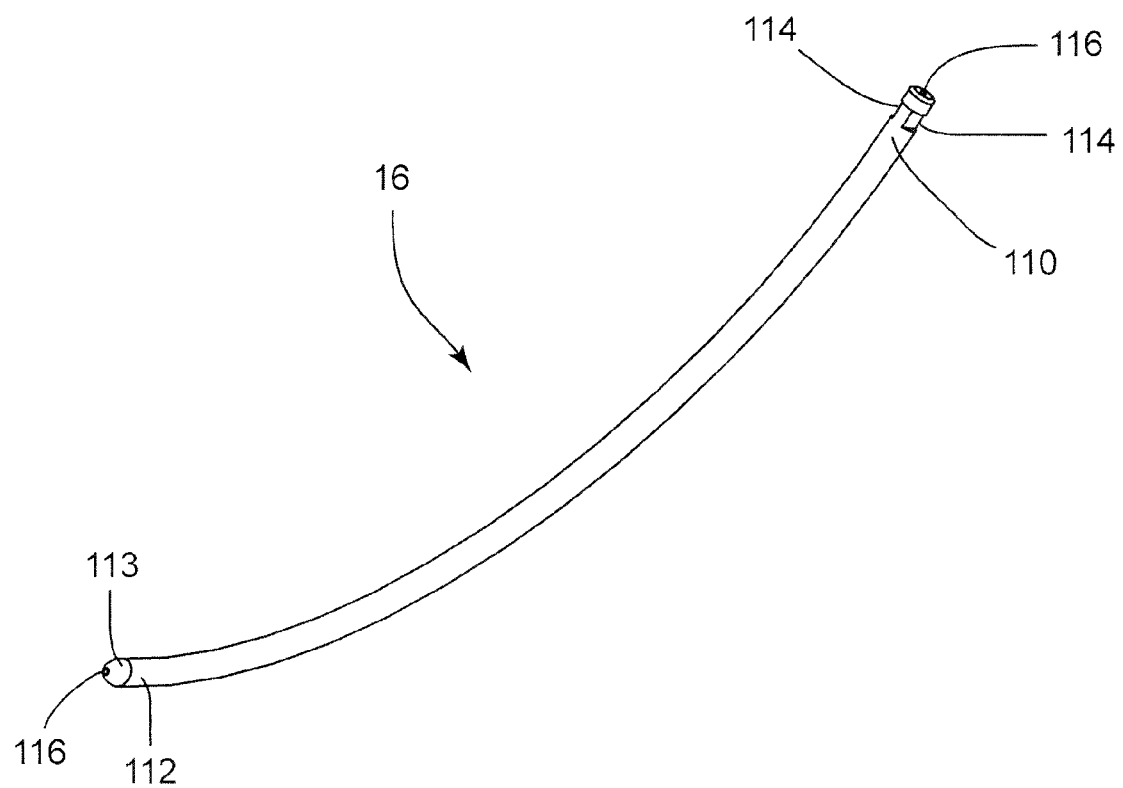
FIG. 5 is a perspective view of a guide member of the arcuate cannula assembly of FIG. 1.

Referring to FIG. 5, the penetrating guide member 16 is shown. The guide member 16 is curved and may be arcuate (i.e., may extend along a fixed radius of curvature). The guide member 16 has a proximal end 110, and a distal end 112 with an insertion tip 113. The insertion tip 113 may be rounded or optionally pointed, to penetrate muscles and fascia. Two attachment recesses 114 at the proximal end facilitate attaching the guide member 16 to the guide arm 14, and are also configured to connect to an instrument support arm. A narrow channel may optionally extend the length of the guide member 16, sized to receive a wire for nerve monitoring or EMG during dilation.

Figure 6A:
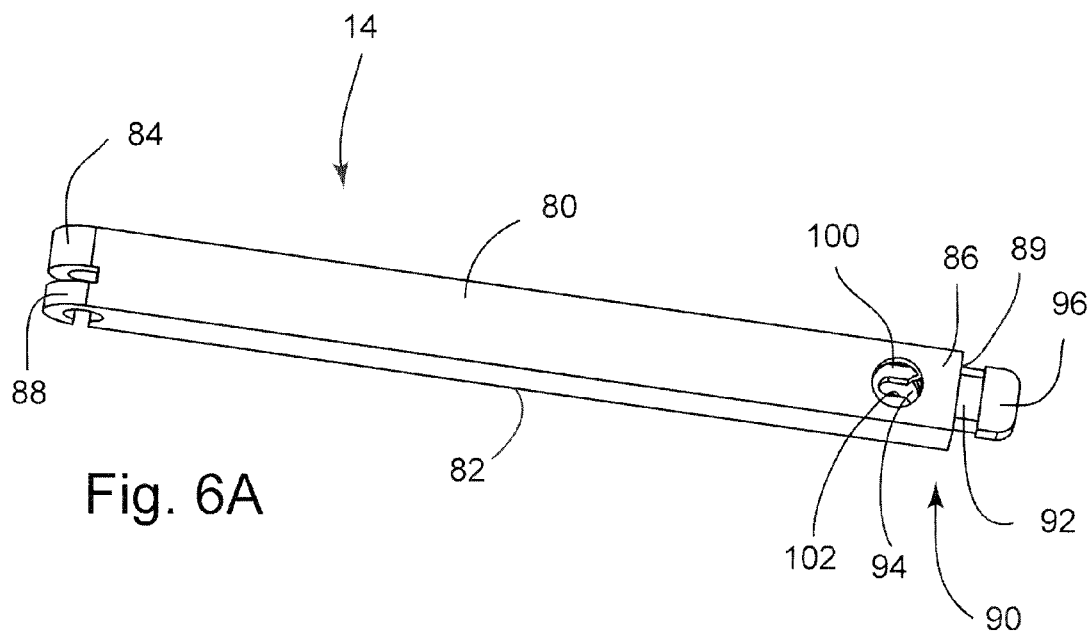
FIG. 6A is a perspective view of a guide arm of the arcuate cannula assembly of FIG. 1.

Referring to FIG. 6A, a perspective view of the guide arm 14 is shown. The guide arm 14 has a first side 80 and a second side 82. At a proximal end is a pinned end 84; a latch end 86 is at the opposite distal end. The pinned end 84 has an attachment feature 88 which is shaped to rotatably attach to the rotation post 50 on the targeting post 12. Inserted into a horizontal slot 89 in the latch end 86 is a spring loaded guide member latch assembly 90 which is shaped to grip the penetrating guide member 16. The guide member latch assembly 90 has a sliding latch bar 92 with a keyhole 94 and a tab 96. On the first side 80 of the guide arm 14, near the latch end 86 is a round guide member opening 100. Directly opposite it on the second side 82 may optionally be a smaller pinhole opening 102.

Figure 6B:
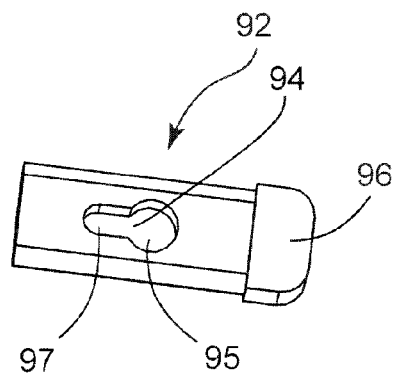
FIG. 6B is a perspective view of a sliding latch bar of the guide arm of FIG. 6A.

FIG. 6B is an enlarged view of the sliding latch bar 92. Keyhole 94 has a rounded lobe 95 disposed toward the tab 96, and an ovoid lobe 97 opposite the tab 96. The rounded lobe 95 is sized to fit around the proximal end 110 of the guide member 16. The ovoid lobe 97 is sized to hold the attachment recesses 114 of the guide member 16. The tab 96 may be grasped to move the sliding latch bar 92 within the horizontal slot 89. A spring (not shown) is disposed in the horizontal slot 89 to provide resistance against the sliding latch bar 92.

Figure 7:
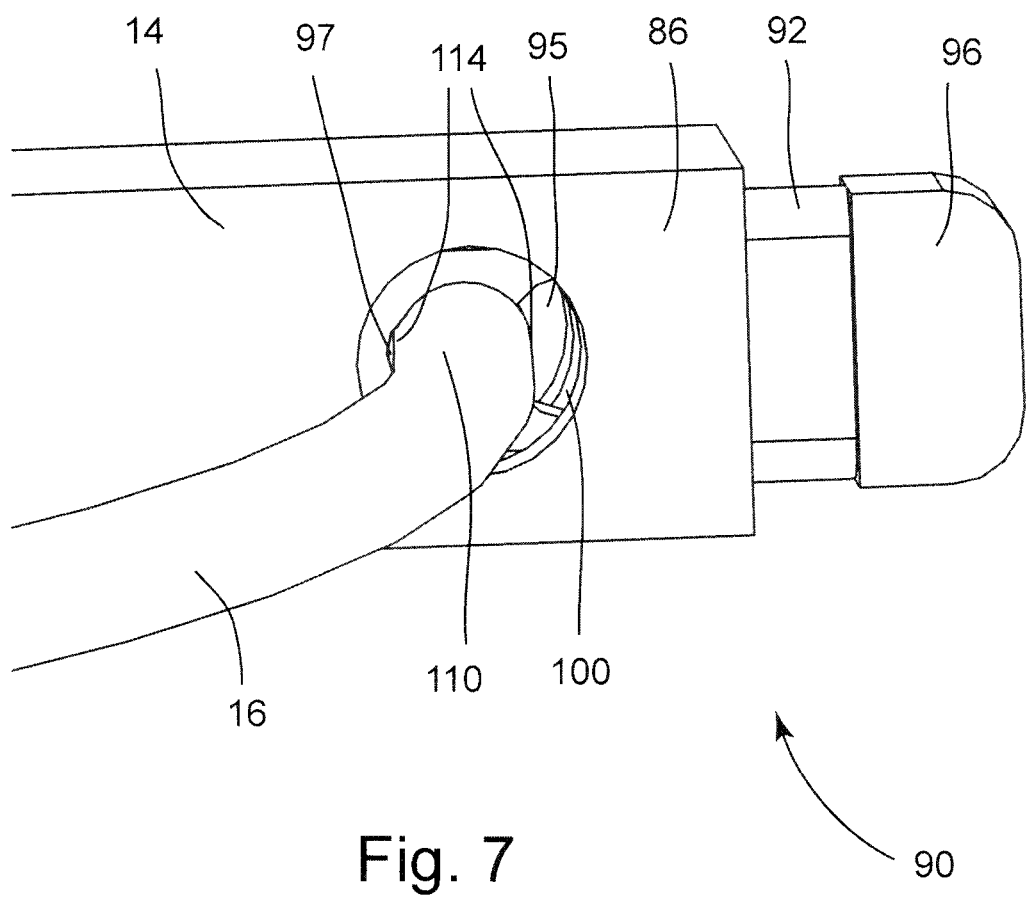
FIG. 7 is a perspective view of a latch assembly of FIG. 6A, with the guide member of FIG. 5 latched thereto.

FIG. 7 is an enlarged view of the latch end 86 of the guide arm 14, showing the guide member 16 latched in the latch assembly 90. To latch the guide member 16 in the latch assembly 90, first the sliding latch bar 92 is introduced into the horizontal slot 89 until the rounded lobe 95 of the keyhole 94 lines up with the guide member opening 100. The proximal end 110 of the guide member 16 is inserted such that the attachment recesses 114 are adjacent to the lined up keyhole 94 and opening 100. The sliding latch bar 92 is released, and the spring (not shown) pushes the sliding latch bar 92 distally until the ovoid lobe 97 of the keyhole 94 slides around the attachment recesses 114 of the guide member 16. The force of the spring traps the guide member 16 in the latch assembly 90, as the guide member is pinned between the ovoid lobe 97 and the latch end 86 of the guide bar 14 adjacent the guide member opening 100.

Figure 8:
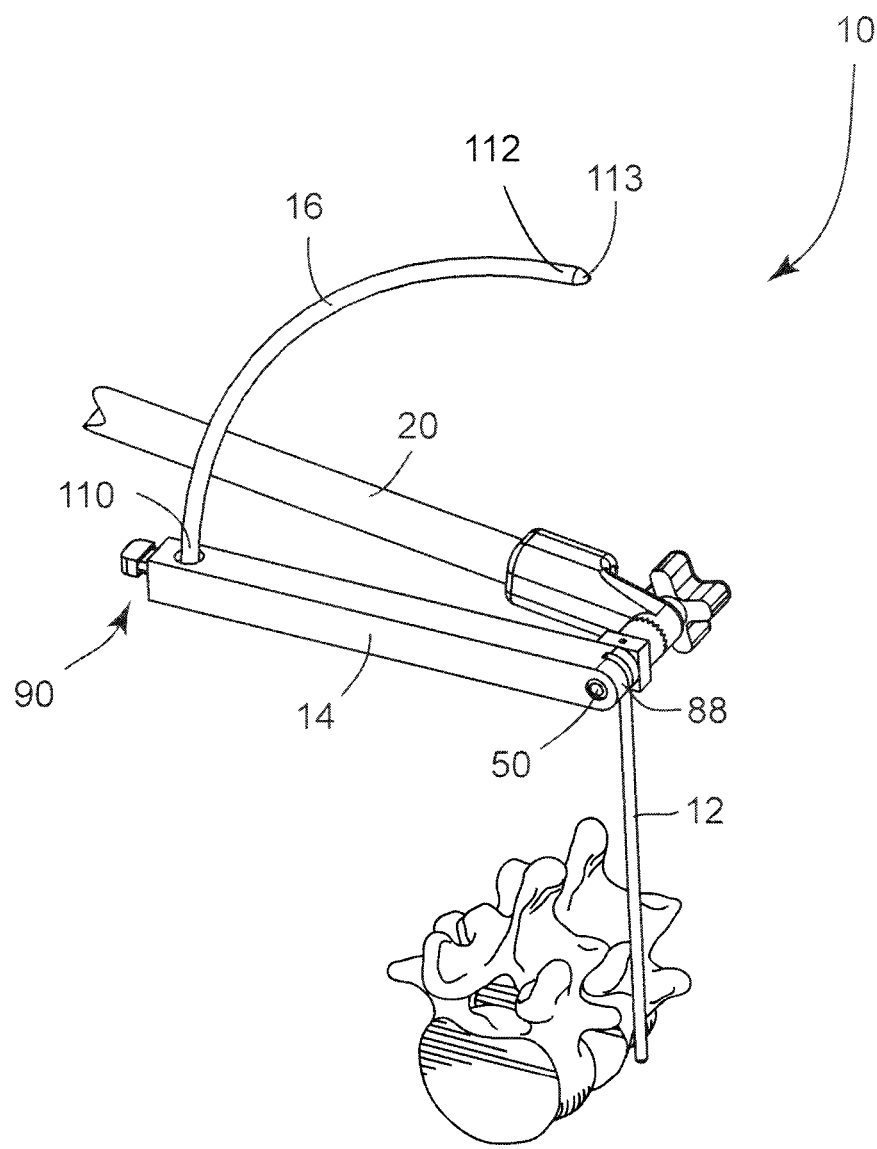
FIG. 8 is a perspective view of the arcuate cannula assembly of FIG. 1 with the guide arm in a first position, adjacent a portion of the spine.

Referring to FIG. 8, the support arm 20, targeting post 12, guide arm 14 and penetrating guide member 16 are shown, with the guide arm 14 and penetrating guide member 16 in a first position. The attachment feature 88 on the guide arm 14 is engaged with the rotation post 50 on the targeting post 12. Thus attached, the guide arm 14 can rotate about the axis of the rotation post 50; however the stop feature 52 on the rotation post 50 may prevent the guide arm 14 from rotating entirely about the rotation post 50. The guide arm 14 may be sized to match the radius of the curve of the penetrating guide member 16, such that the arc centerpoint of the penetrating guide member 16 is coincident with the center of rotation, or axis of the rotation post 50. The guide member latch 90 holds the penetrating guide member 16 as seen in FIG. 7.

After the penetrating guide member 16 is attached to the guide arm 14, the guide arm 14 is rotated so that the insertion tip 113 of the guide member 16 makes contact with the skin. Optionally, an incision location may be marked on the skin. At this point, the guide member 16 is lifted and an incision of approximately 1-5 cm is made into the skin and fascia. Following the incision, the surgeon may insert a finger into the incision to locate and palpate the soft tissues and fascia.

Figure 9:
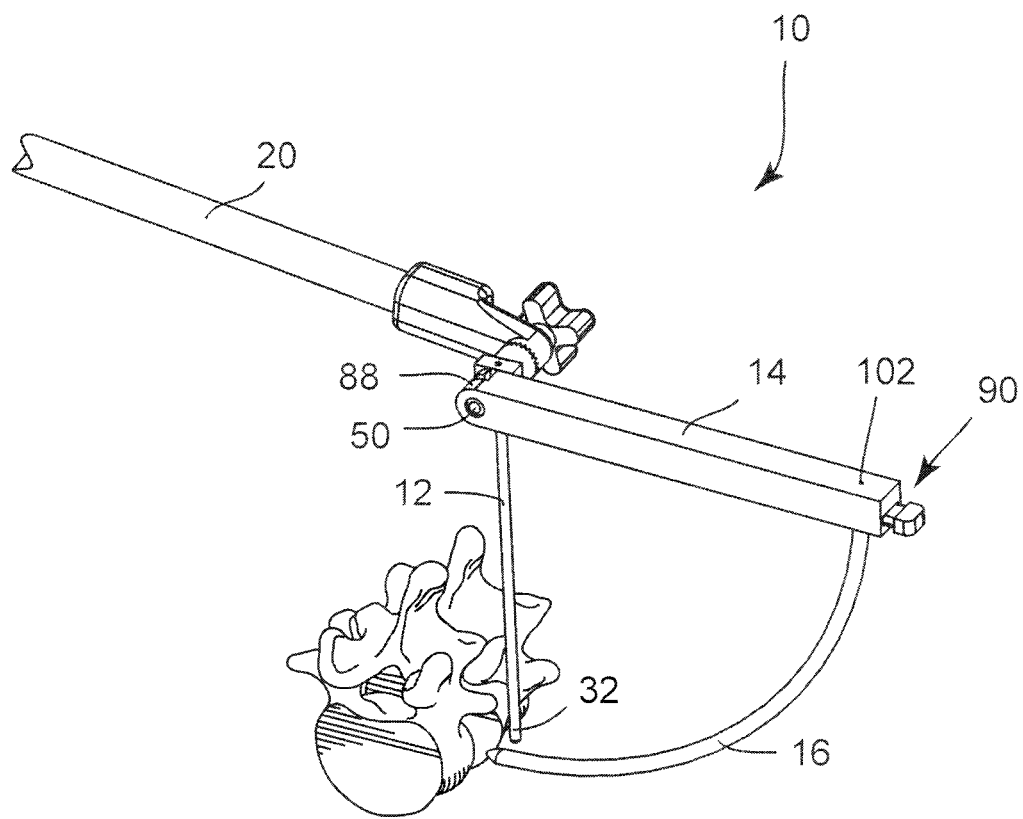
FIG. 9 is a perspective view of the arcuate cannula assembly of FIG. 1 with the guide arm in a second position, adjacent a portion of the spine.

As shown in FIG. 9, the guide member 16 is then advanced into the incision via rotation of the guide arm 14. The guide member is advanced antero-medially along the arcuate path until the insertion tip 113 is at the lateral margin of the targeted disc, at a target location. The target location is at a known position relative to the reference location provided by the distal end 32 of the targeting post 12, as the guide bar 14 holds the guide member 16 in a fixed relationship as the guide bar 14 rotates about the rotation post 50. At this point the guide arm and guide member are in a second position. The guide member 16 may have a rounded insertion tip, or a sharp, pointed insertion tip if necessary to penetrate the tissues. EMG monitoring may be used to ensure safe passage of the guide member through the fascia. The optional pinhole opening 102 creates access for a wire to pass through the guide arm into the guide member 16 if it is desirable to connect an electrode to the guide member 16 for nerve monitoring. The stop feature 52 (seen in FIG. 2) stops rotation of the guide arm 14 and prevents the guide member 16 from extending past the margin of the disc and contacting the spinal cord. The penetrating guide member 16 may vary in length and radius of curvature, to accommodate differing patient proportions and differing specific target locations. Accordingly, the guide arm 14 may be adjustable in length, to function correctly with the guide member to reach the target location.

Once the guide member 16 is correctly positioned adjacent the targeted location, the guide arm 14 is detached from the guide member 16 and the targeting post 12. The guide member 16 is left in the patient to serve as a guide for one cannula or series of cannulas which are graduated in size, and which are inserted sequentially from smaller to larger to increase the cross-sectional area of the access portal to the area to be treated.

Figure 10:
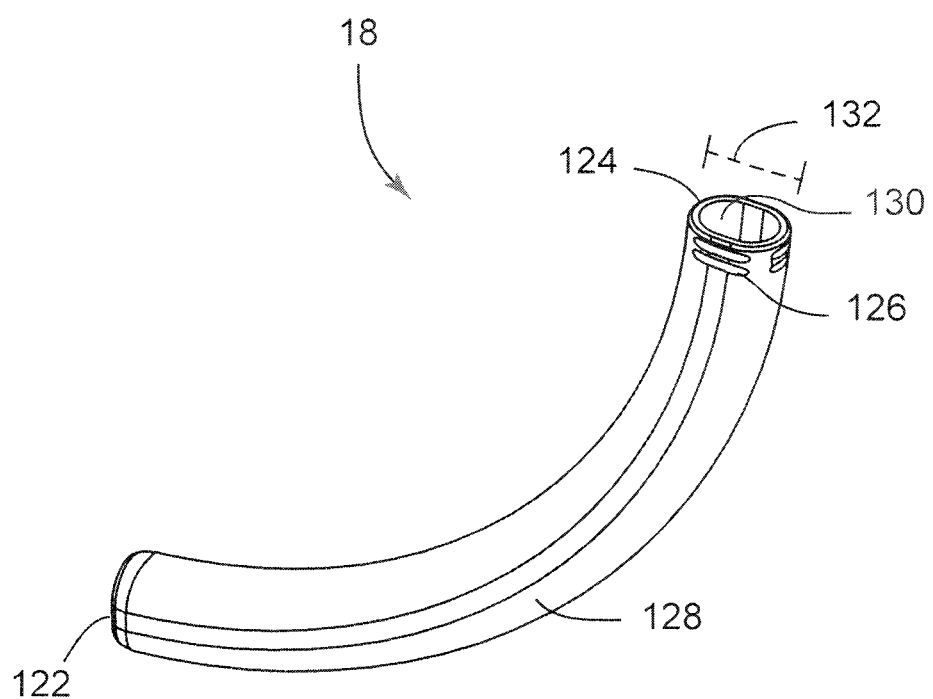
FIG. 10 is a perspective view of a cannula.

Referring to FIG. 10, a single cannula 18 is shown. The cannula 18 is longitudinally curved and generally tubular in form, with a tubular support wall 128 which has an open distal end 122 and an open proximal end 124. The distal end 122 is rounded so that tissues are pushed aside gently as the cannula is inserted through the patient. A bore 130 runs the length of the cannula 18 from the open distal end 122 to the open proximal end 124, and provides access to the targeted spinal area for instrument insertion, and insertion and removal of interbody devices, arthroscopic devices, implants, bone graft materials, bone cement, and other materials and devices. A cross-sectional shape of the support wall 128 of the bore 130 is generally curved, and may specifically be round, oval, elliptical or another curved shape. The cross-sectional shape has a width 132, which may have a maximum measurement of about 27 millimeters. The open proximal end 124 has a plurality of grip features 126 which allow the surgeon to grip the cannula. Optionally, the cannula 18 may have attachment features to allow attachment of the cannula to the instrument support arm. The cannula 18 may optionally be substantially radiolucent, and can comprise biocompatible polymers, elastomers, ceramics, or aluminum or other metals. The longitudinal curve of the cannula 18 may be arcuate, and may sweep through an angle of about 90° such that the open proximal and distal ends 124, 122 are substantially perpendicular to each other. A radius of curvature of the cannula may be constant along the entire cannula, and may range from about 2 to about 9 inches.

Figure 11:
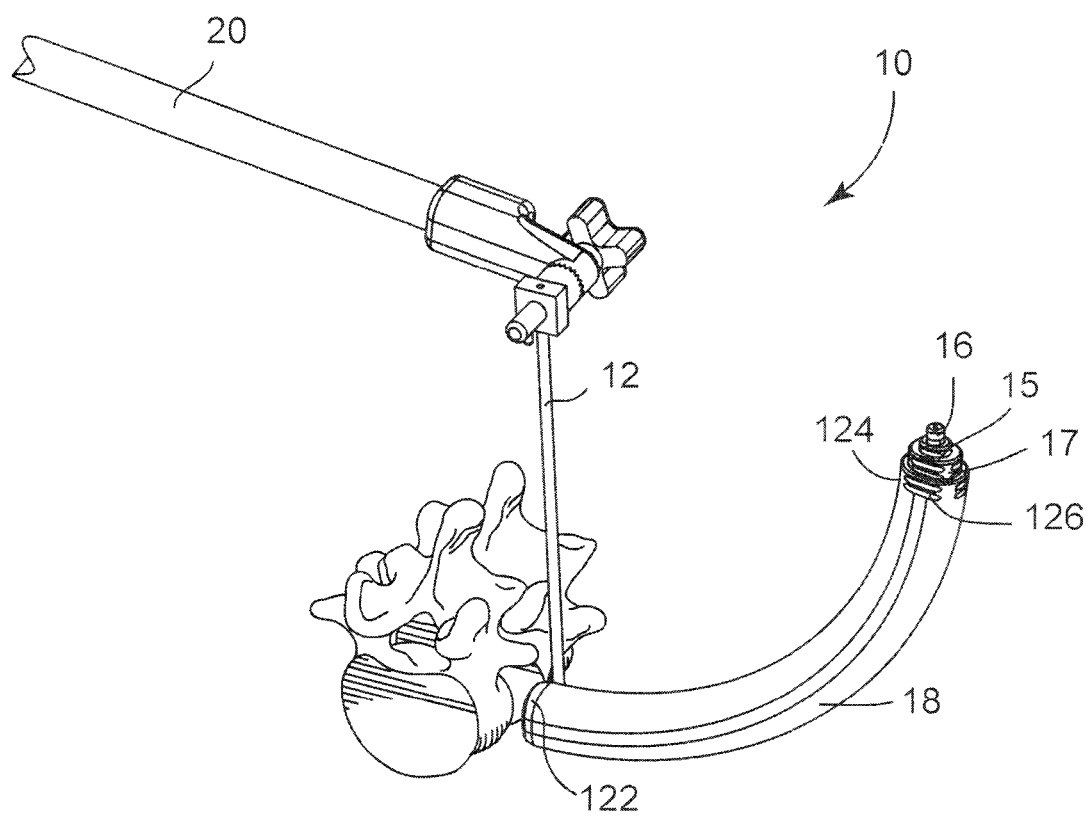
FIG. 11 is a perspective view of the arcuate cannula assembly of FIG. 1 with the guide arm removed and several cannulas added, adjacent a portion of the spine.

Referring to FIG. 11, a series of graduated cannulas 15, 17, 18 are inserted one at a time over the proximal end 110 of the penetrating guide member 16, and advanced antero-medially over the guide member 16 until the corresponding distal end reaches the distal end 112 of the guide member 16. Each cannula 17, 18 is shorter in length and larger in cross-sectional area than the next smallest cannula, to allow the surgeon to grip each cannula as it is installed and removed. As each cannula 15, 17, 18 is inserted, the access portal through the soft tissues and fascia is increased in size, creating increased access to the targeted portion of the spine. The number of cannulas inserted is determined by the desired cross-sectional area of the opening to the spine; in many instances two to five cannulas will be inserted. Once all cannulas 15, 17, 18 are inserted around the penetrating guide member 16, the guide member 16 and the inner cannulas 15, 17 are removed, leaving the largest cannula 18 in the patient. This cannula may be attached via an attachment feature (not shown) to the support arm 20, to provide additional stabilization for removal of the smaller cannulas, and for subsequent instrument insertion and procedures.

In one embodiment of the invention, the largest cannula 18 may have a tooth portion (not shown) which extends longitudinally from the insertion end 122. During insertion, the tooth portion is placed between the superior and inferior endplates of the intervertebral space, to assist in maintaining distraction and access to the space. In an alternative embodiment, the largest cannula 18 may have one or more protruding pins or other elements extending from the insertion end 122 which can penetrate the superior and/or inferior vertebral bodies to provide additional stability to the cannula 18.

Figure 12:
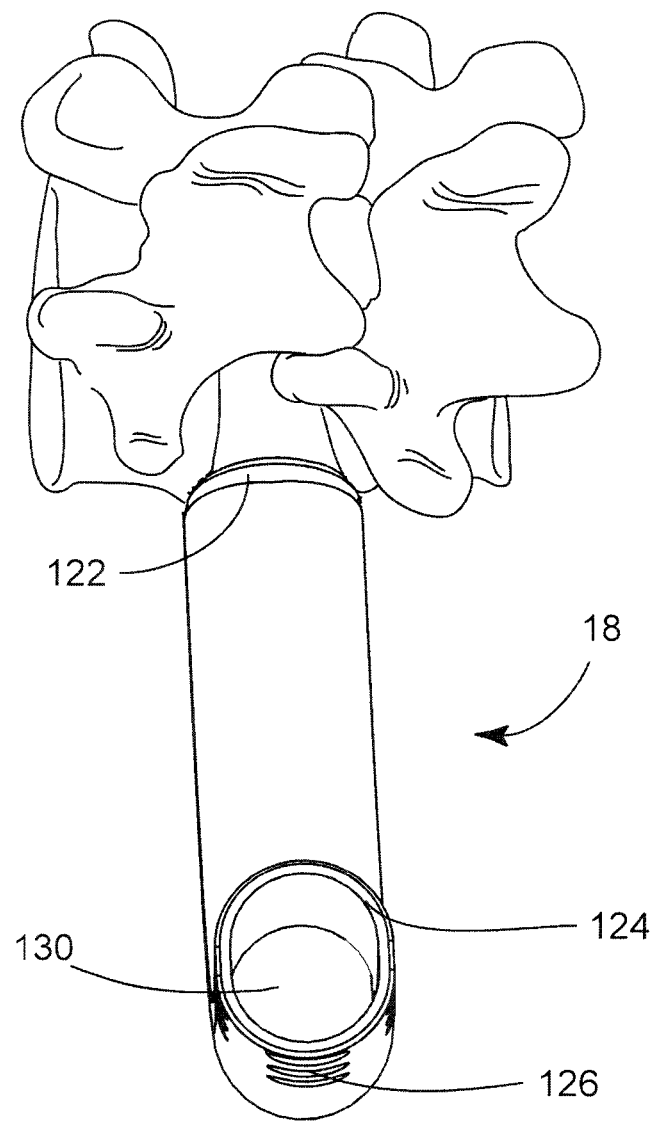
FIG. 12 is a postero-lateral perspective view of the cannula of FIG. 10 adjacent a portion of the spine.

FIG. 12 is a postero-lateral view of a portion of a spine with a cannula inserted according to the procedure previously described. When in place in the patient, the bore 130 of the cannula 18 is an access portal through which surgical instruments, implants and other materials may be passed to complete a variety of intervertebral procedures. Surgical instruments used in conjunction with the cannula 18 may have rigid, curved shafts or flexible shafts to navigate through the cannula 18 to the intervertebral space. The cannula 18 may be sized to accommodate passage of an interbody fusion implant 300 (shown in FIGS. 15A and 15B).

Figure 13:
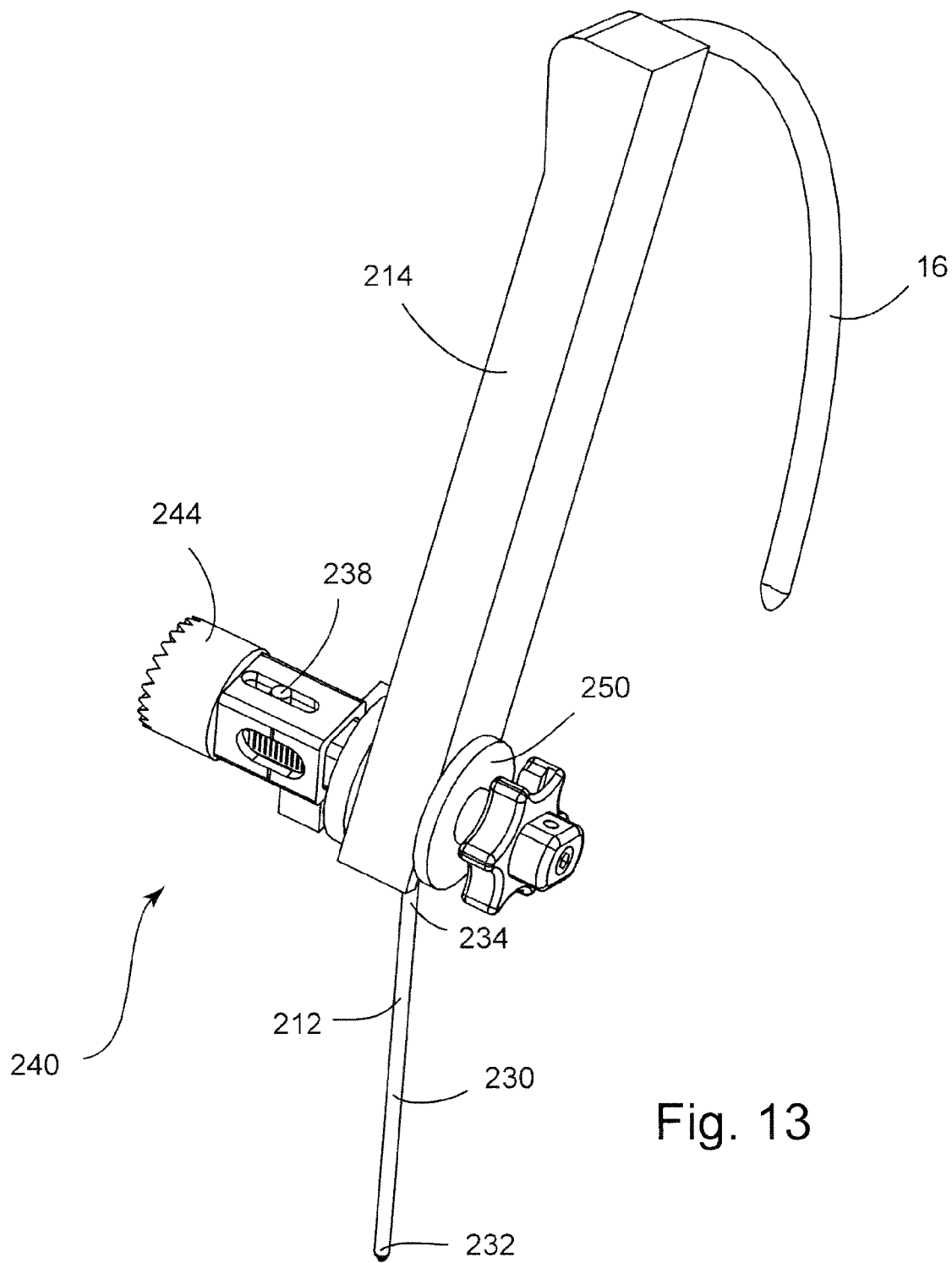
FIG. 13 is a perspective view of an arcuate cannula assembly with an adjustable targeting post.

Another embodiment of the invention comprises a targeting post which is capable of cephalad-caudal adjustment. FIG. 13 is a perspective view of an arcuate cannula assembly 210 which includes an adjustable targeting post 212, a guide arm 214 and a penetrating guide member 16. The adjustable targeting post 212 has a shaft 230 which has a distal end 232 and a proximal end 234. Proximally adjacent to the proximal end 234 of the shaft 230 is a connection portion 240, which extends in a cephalad-caudal direction and comprises a guide arm connector 250, a cephalad-caudal adjustment feature 238, and a support arm attachment post 244. The cephalad-caudal adjustment feature 238 can be adjusted to lengthen or shorten the cephalad-caudal length of the connection portion 240. Thus, after the targeting post is inserted into the patient, the length of the connection portion 240 can be adjusted as necessary to attain the necessary offset to adjust the resultant cephalad-caudal distance between the guide member 16 and the targeting post 212. The adjustment allows the target location to vary along the cephalad-caudal direction such that the known position of the target location is offset relative to the reference location. Cephalad-caudal offset of the guide arm 214 and the attached guide member 16 may be useful in avoidance of nerve structures and other objects during the dilation process.

Figure 14:
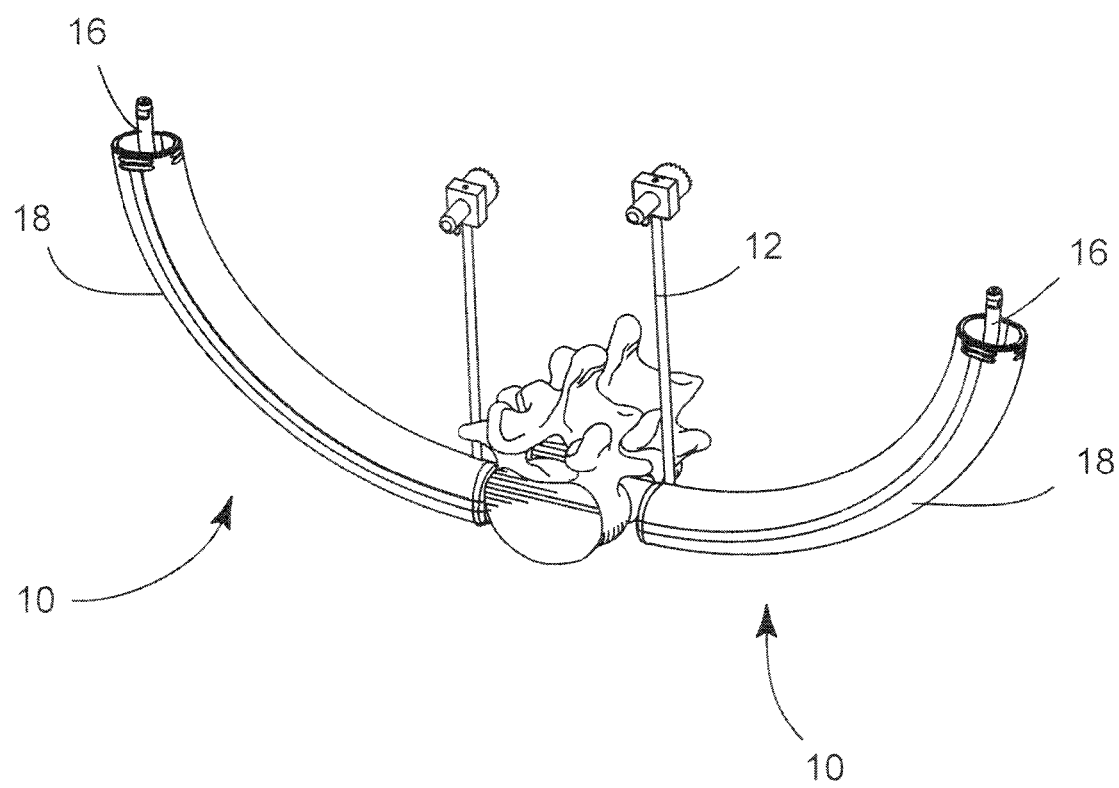
FIG. 14 is a perspective view of two arcuate cannula assemblies of FIG. 1, adjacent two lateral sides of a portion of the spine.

Another application of the invention comprises a bilateral implementation of two arcuate cannula assemblies. In this embodiment, two assemblies 10 are used together, one on each lateral side of the spine. Referring to FIG. 14, portions of two assemblies 10, which comprise two targeting posts 12, two penetrating guide members 16, and two cannulas 18, are shown adjacent to each lateral side of the spine. This embodiment permits enhanced access to the targeted area, since access may be attained from both lateral sides simultaneously. Instruments, implants, or other materials may be pushed or pulled into the intervertebral space, or through the entire access pathway.

Figure 15A:
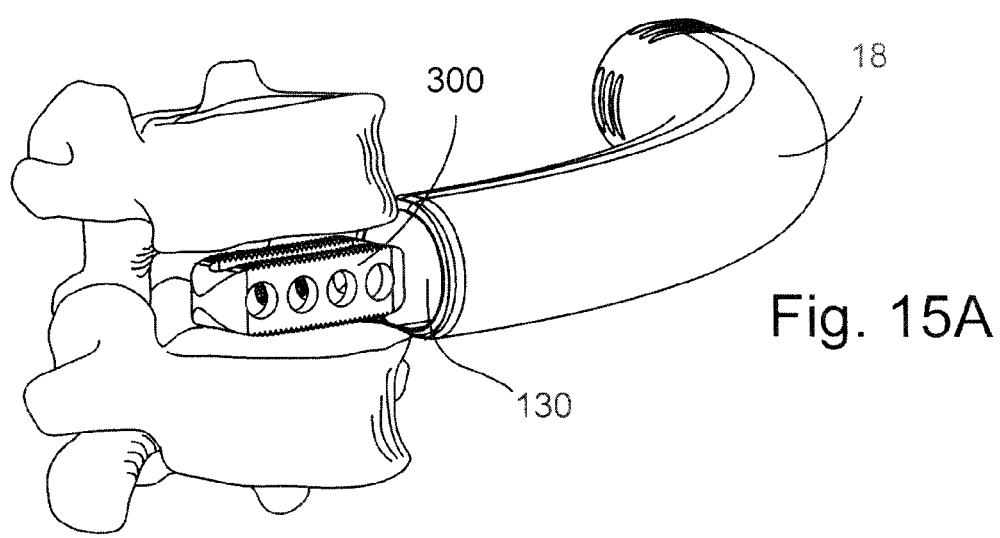
FIG. 15A is an antero-lateral perspective view of the cannula of FIG. 10 adjacent a portion of a spine, and an interbody device in an intervertebral space.
Figure 15B:
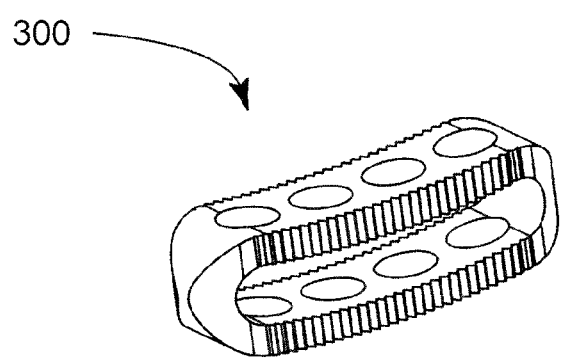
FIG. 15B is a perspective view of the interbody device of FIG. 15A.

Another embodiment of the invention further comprises an implant, which may be an interbody device. FIG. 15A is an anterior perspective view of first and second vertebrae with a cannula 18 and an interbody device 300 which may be inserted through the arcuate cannula assembly previously disclosed. An implant retaining inserter with a curved shaft (not shown) may be used to move the implant along the arcuate pathway of the cannula, then release the implant in the interbody space between the vertebrae. FIG. 15B is a perspective view of the interbody device 300 of FIG. 15A. The interbody device 300 has a generally rectangular box-like shape, and is slightly curved along its longitudinal axis. The interbody device 300 may optionally have a radius of curvature substantially the same as that of the cannula 18.

Other implants (not shown) may be shaped to be implantable through the cannula in the manner set forth previously and illustrated in FIG. 15A. These implants may include, but are not limited to, a nucleus replacement, an annulus replacement, a staple, a lateral plate, a lateral plate-interbody implant combined device, an artificial disc, a therapeutic-containing implant, a vertebral body screw, a vertebral body anchor, and a facet replacement.

In any case, the bore 130 of the cannula 18 is sized to accommodate passage of the interbody device 300. Because use of the arcuate cannula assembly 10 allows improved access to the intervertebral space, the interbody device 300 may have a larger footprint than many other interbody devices, and can extend across most of the medial-lateral width of the intervertebral space, to provide for increased stability, increased bone in-growth, and improved fusion. A curved insertion tool and curved tamp (not shown) are used to insert and seat the interbody device 300 in the intervertebral space. In the alternative, a flexible insertion tool and/or a flexible tamp may be used.

A set of curved spinal orthopedic instruments may be used in conjunction with the arcuate cannula assembly set forth previously to complete spinal procedures. These instruments are set forth below and in FIGS. 17-27, and may include rasps, curettes, rongeurs, wedge distractors, trial implants, tamps, probes and implant insertion devices, among others. Each instrument may have a gripping portion, and a working portion which comprises a shaft and a specific tool portion, or working end. The shaft may be an arcuate shaft which extends along an arcuate shaft pathway that matches the pathway along which the corresponding cannula extends. The working end of each instrument is sized to pass through the arcuate cannula 18, and may be coupled to the arcuate shaft such that the working end follows the same trajectory as the arcuate shaft; thus the entire working portion may be continuously curving along the arcuate shaft pathway. The radius of curvature of the arcuate shaft pathway may substantially equal the radius of curvature of the arcuate cannula 18. Thus configured, the working portion of each instrument may be inserted through the arcuate cannula, allowing the working end to protrude out of the distal end of the cannula to reach the location of the spinal procedure.

Figure 16:
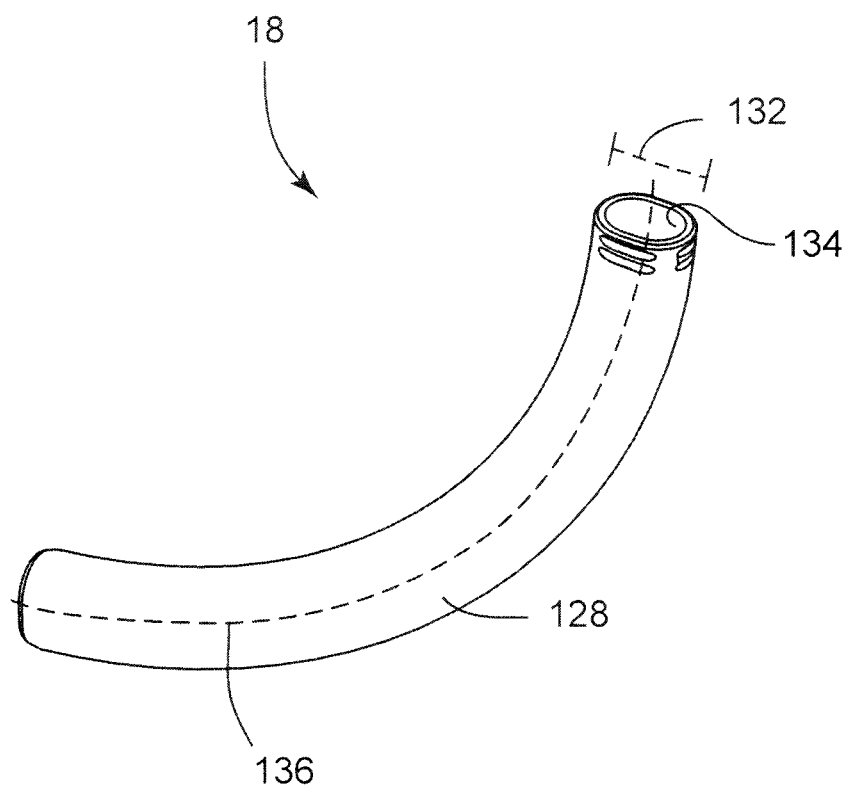
FIG. 16 is a perspective view of the cannula of FIG. 10, showing the boundaries of an arcuate envelope.

Referring to FIG. 16, a perspective view of the cannula 18 is shown. The cannula 18 is curved, and, as embodied in FIG. 16, is also arcuate. Thus, the cannula 18 defines an arcuate envelope through which an instrument may pass. The cannula 18 (and thus the arcuate envelope) extends longitudinally along an arcuate envelope pathway 136, which may have a radius ranging from about 2 inches to about 12 inches. More precisely, the arcuate envelope pathway may have a radius ranging from about 4 inches to about 9 inches. Still more precisely, the arcuate envelope pathway may have a radius of about 5.5 inches. The support wall 128 which forms the cannula has an interior surface 134. As mentioned previously, the interior surface 134 defines the arcuate envelope. The arcuate envelope, and thus the cannula 18, extends longitudinally along the arcuate envelope pathway 136, and may sweep through an arc ranging from about 45° to about 135°. More precisely, the cannula 18 may sweep through an arc ranging from about 60° to about 120°. Yet more precisely, the cannula 18 may sweep through an arc ranging from about 75° to about 105°. Still more precisely, the cannula 18 may sweep through an arc of about 90°.

The cannula 18 (and hence the corresponding envelope) has a substantially uniform cross-sectional shape, which may be circular, ovoid, elliptical or any other uniform, closed shape. A "substantially uniform cross-sectional shape" is possessed by an "extrusion," i.e., a body that extends along a pathway with substantially the same cross-sectional shape and size (taken perpendicular to the pathway) at any location along the length of the pathway. The maximum width of the arcuate envelope, defined as a straight line across the largest dimension of the cross-section taken at right angles to the arcuate envelope pathway 136, may range from about 5 millimeters to about 50 millimeters. More precisely, the maximum width may range from about 15 millimeters to about 40 millimeters. Yet more precisely, the maximum width may range from about 20 millimeters to about 30 millimeters. Still more precisely, the maximum width of the arcuate envelope may be about 27 millimeters. The arcuate shaft and working end of each instrument are configured and coupled together such that they may pass through the arcuate envelope and the working end may extend out of the envelope.

Figure 17:
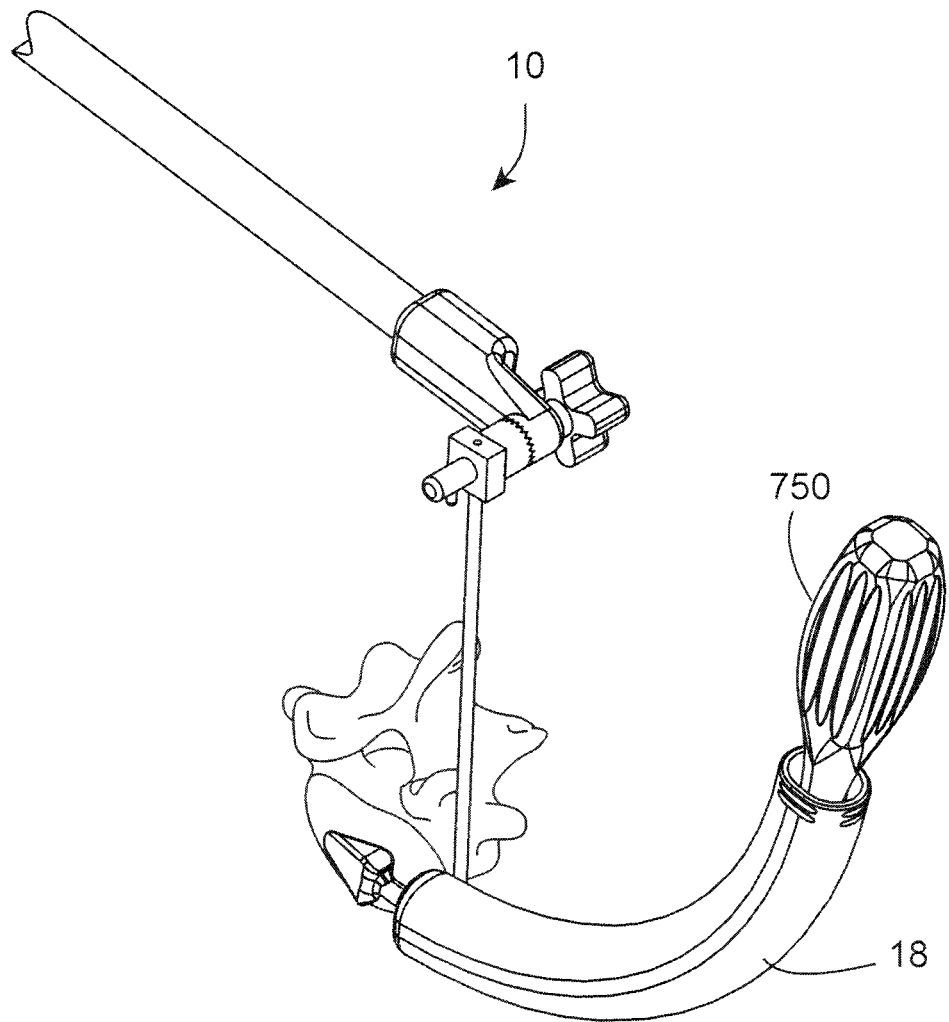
FIG. 17 is a perspective view of an arcuate cannula assembly with a curved wedge distractor instrument inserted into a cannula, adjacent a portion of the spine.

In FIG. 17, an instrument with a curved shaft is inserted through the arcuate cannula 18 of the arcuate cannula assembly 10 to reach the location of a spinal procedure. One vertebra is shown to provide perspective; a second is omitted so that a working end of the instrument may be seen. Wedge distractor 750, similar to wedge distractor 700 described below but with a different wedge head, is inserted through cannula 18 to reach the intervertebral space. A working portion of the wedge distractor 750 comprises a working end, in this case the wedge head, and a shaft that couples the working head to a handle. The arcuate shaft is may be curved, and may indeed be curved along a constant radius to provide an arcuate shaft that passes through the arcuate envelope defined by the interior surface of the arcuate cannula 18.

Figure 18:
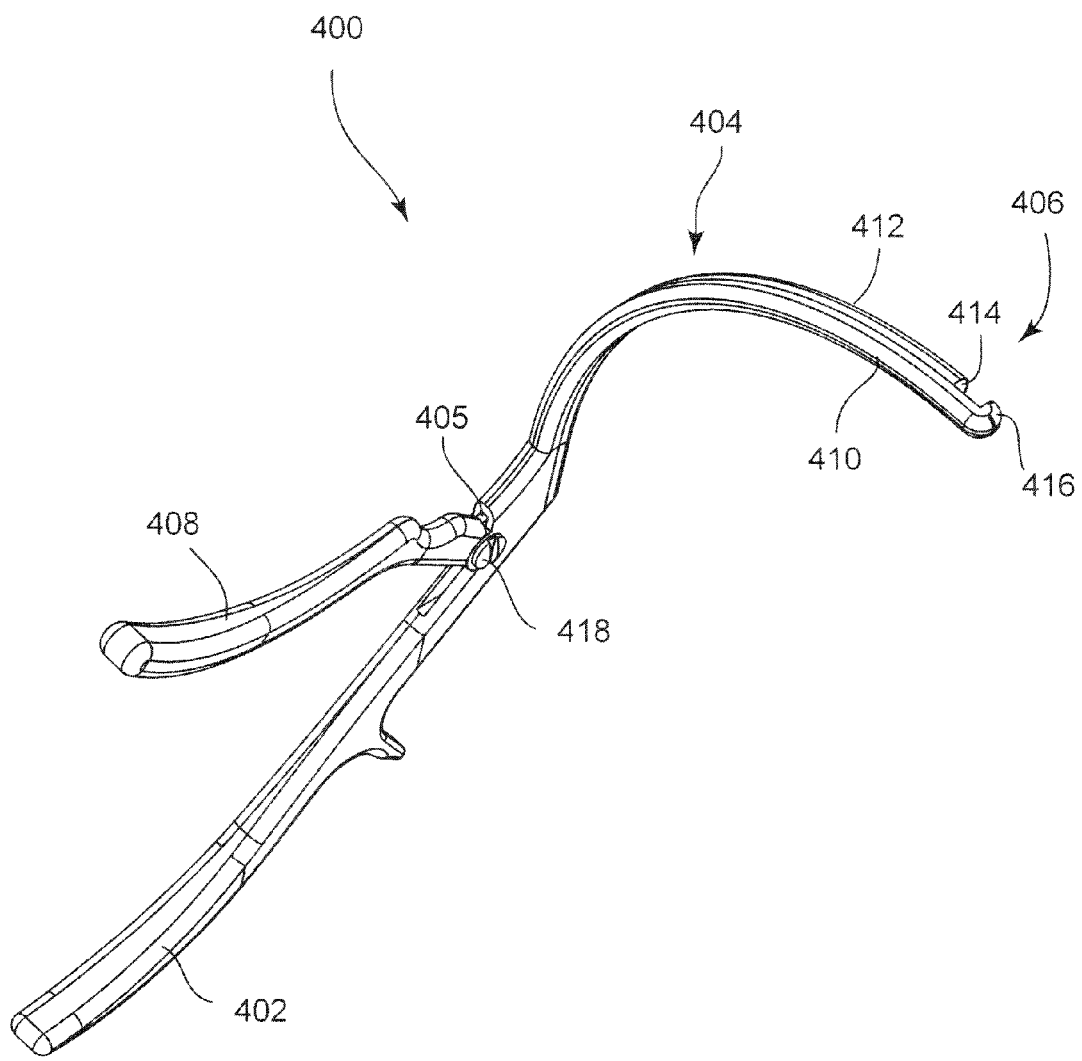
FIG. 18 is a perspective view of a curved rongeur.

Referring to FIG. 18, a perspective view of a curved rongeur 400 is shown. The curved rongeur 400 has a gripping portion 402 with an adjacent lever 408, and a working portion consisting of a curved shaft 404 and a working end in the form of a nipping mechanism 406. Coupled to the gripping portion 402 is the proximal end of the curved shaft 404 which extends along an arcuate shaft pathway. Coupled to the distal end of the arcuate shaft 404 is the nipping mechanism 406. The curved shaft 404 has two longitudinally oriented arcuate elements, a shank 410 and a crossbar 412. The shank 410 extends from the gripping portion, and terminates distally at a stop 416. The crossbar 412 is connected to the lever 408 by a link 405. A pivot 418 connects the lever 408 to the gripping portion 402, such than as the lever 408 is actuated, the lever 408 rotates about the pivot 418 and the linked crossbar 412 slides along the shank 410. The nipping mechanism 406 comprises a distal end 414 of the crossbar 412, and the stop 416. When the lever 408 is fully actuated, the crossbar 412 slides along the shank 410 until the distal end 414 of the crossbar 412 meets the stop 416.

During a surgical procedure, the curved rongeur 400 may be inserted through an arcuate cannula such as the arcuate cannula 18 of FIG. 16, and the nipping mechanism 406 may be employed through manipulation of the gripping portion 402 and lever 408 to grasp and relocate pieces of bone, cartilage, intervertebral disc tissues, or other tissues or materials. The curved shaft 404 is narrow and long enough that the nipping mechanism 406 can reach a variety of locations at the targeted area, such as in an interbody space between two vertebrae.

Figure 19:
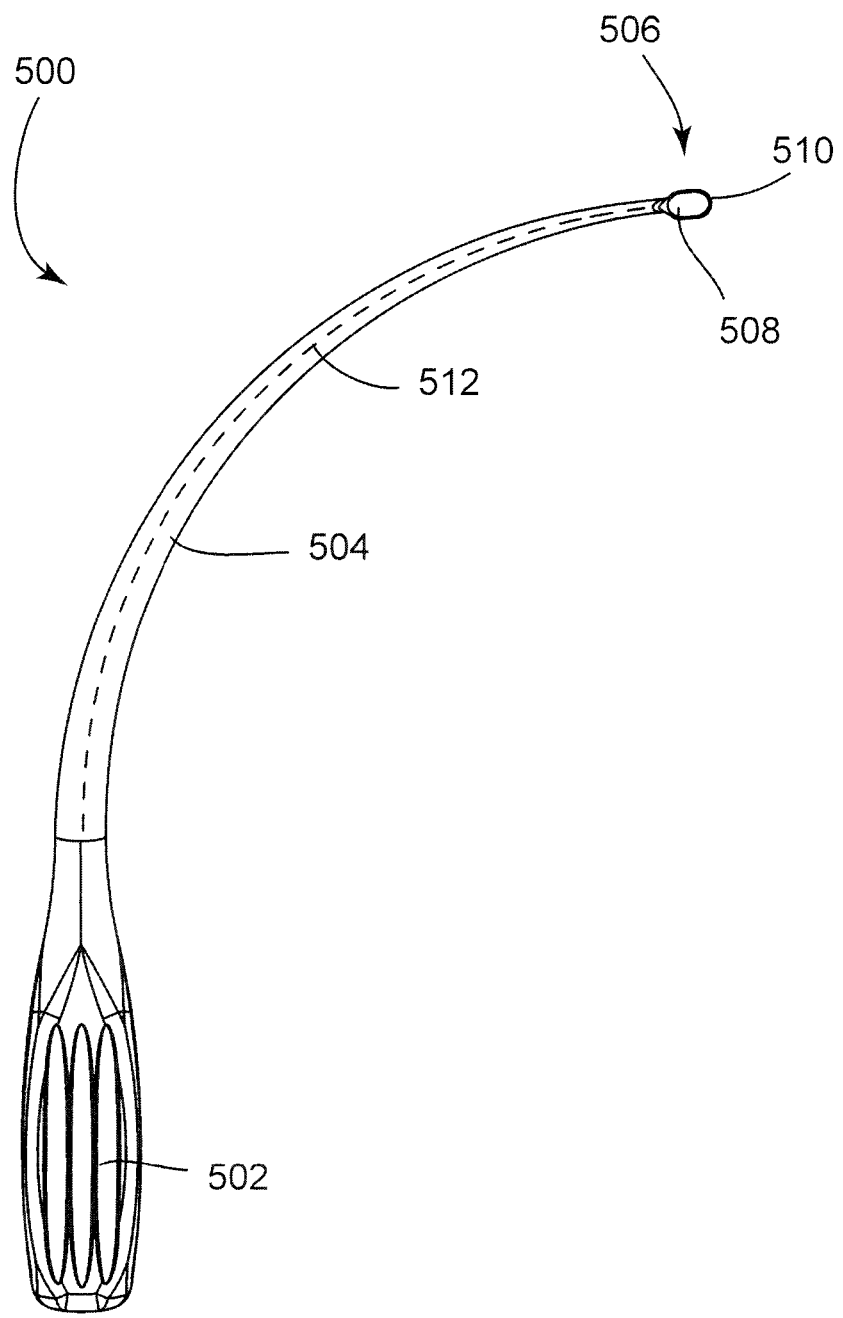
FIG. 19 is a perspective view of a curved curette.

Referring to FIG. 19, a perspective view of one embodiment of a curved curette 500 is shown. The curved curette 500 has a gripping portion 502 to which is coupled an arcuate shaft 504 which extends along an arcuate shaft pathway 512. The arcuate shaft pathway 512 may have a radius ranging from about 2 inches to about 12 inches. More precisely, the arcuate shaft pathway 512 may have a radius ranging from about 4 inches to about 9 inches. Still more precisely, the arcuate shaft pathway 512 may have a radius of about 5.5 inches. The curvature of the arcuate shaft pathway 512 may match the curvature of the arcuate envelope pathway 136 (shown in FIG. 16). These dimensions may be applied to any instrument or to any cannula disclosed herein.

Coupled to the distal end of the arcuate shaft 504 is a working end which is a cutting head 506. Cutting head 506 is spoon-shaped, with a cup 508 and a blade 510 forming the rim of the cup. The cutting head 506 may be disposed at a variety of orientations and angles relative to the arcuate shaft 504. In FIG. 19, the cutting head 506 is aligned with the curve of the arcuate shaft 504, and the cup 508 opens upward when the curette 500 is held in a horizontal position as depicted.

Figure 20A:
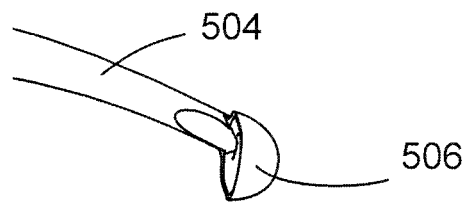
FIG. 20A is a perspective view of a curette head in an upward-opening, angled position.
Figure 20B:
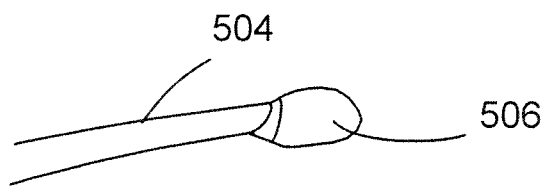
FIG. 20B is a perspective view of a curette head in an downward-opening position.
Figure 20C:
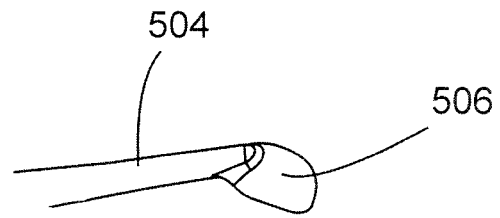
FIG. 20C is a perspective view of a curette head in an downward-opening, angled position.

FIGS. 20A-20C display some of the possible other orientations of the cutting head, which allow the cutting head to reach different areas in the intervertebral space. Each orientation may still allow the cutting head to pass through the arcuate cannula; the cutting head may be small enough that even when oriented at an angle, it still fits within the arcuate envelope defined by the cannula 18. In FIG. 20A, the cutting head 506 opens upward relative to the arcuate shaft 504 and is disposed at an angle to the longitudinal axis of the shaft. In FIG. 20B, the cutting head 506 is aligned with the arcuate shaft 504, and opens downward. In FIG. 20C, the cutting head 506 opens downward and is disposed at an angle to the arcuate shaft 504, but still fits within the arcuate envelope defined by the interior surface of the cannula 18. This variety of orientations allows a surgeon to choose the curette configuration best suited for the particular task at hand. These figures represent only some of the orientations at which the cutting head 506 may be disposed; it is appreciated that many other configurations are possible and are within the scope of the disclosure.

Figure 21:
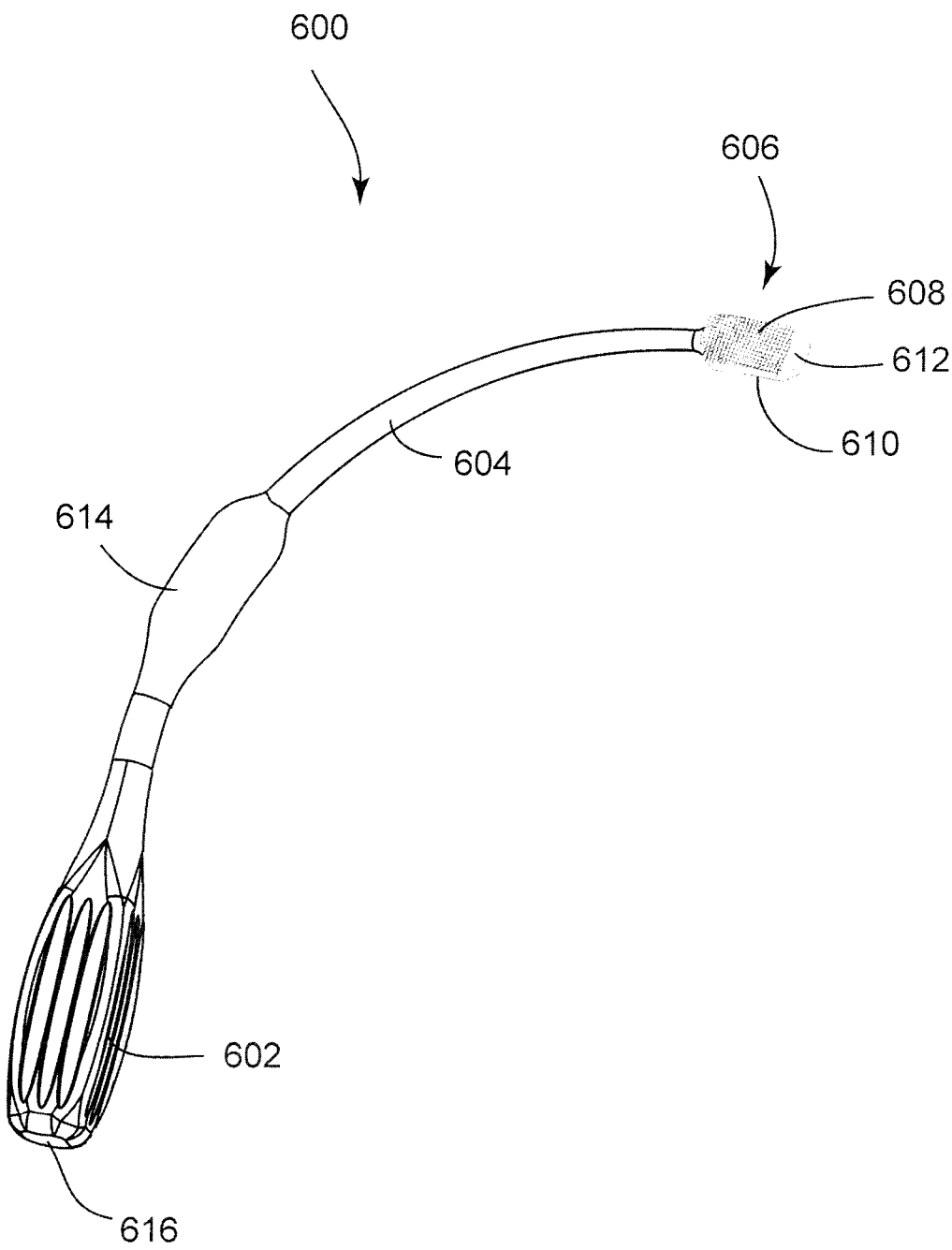
FIG. 21 is a perspective view of a curved wedge rasp.

Referring to FIG. 21, a perspective view of one embodiment of a curved wedge rasp 600 is shown. The curved wedge rasp 600 has a gripping portion 602, an arcuate shaft 604, and a working end which is a rasp head 606, coupled to the distal end of the arcuate shaft 604. The arcuate shaft 604 follows an arcuate shaft pathway similar to the arcuate shaft pathway 512 of the curved curette 500. The arcuate shaft 604 and rasp head 606 make up a working portion which is sized and oriented to fit through an arcuate cannula such as the cannula 18 in the manner set forth previously and depicted in FIG. 17. The rasp head 606 is generally rectangular in shape but curves slightly, following the arcuate envelope pathway 136 (shown in FIG. 16). Alternatively, such a rasp may have a conventional straight rasp head 606 in combination with a curved shaft.

A first toothed rasp surface 608 occupies one long side of the rasp head 606, while a second toothed rasp surface 610 is on the opposite side. A wedge 612 is at the distal terminus of the head 606, allowing the surgeon to pry into and distract the targeted area and then rasp the distracted surfaces. Various dimensions of the rasp head may vary, including the length, height and width of the rasp head 606, size of rasp teeth, and length of the wedge 612, among others. The height of the rasp head may be sized to match the height of an implant, so that the rasp prepares a correctly sized area for insertion of the implant. A stabilization feature 614 is a wide portion of the arcuate shaft 604 and is configured to fit just inside the arcuate cannula 18 to stabilizes the position of the rasp 600 as force is applied to the handle 602. The gripping portion 602 has a reinforced impaction surface 616 at its proximal end to facilitate striking of the gripping portion 602 with an object such as a mallet.

Figure 22:
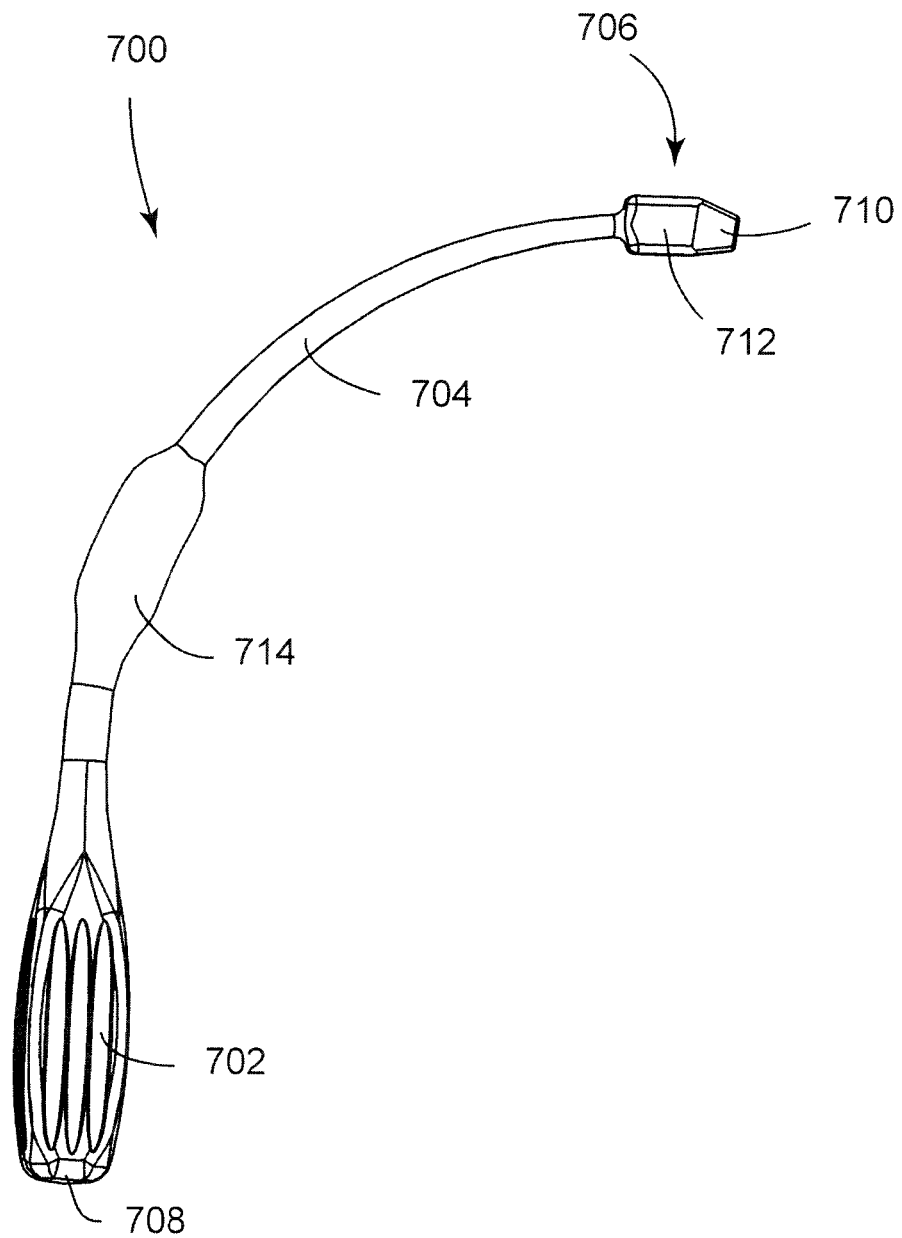
FIG. 22 is a perspective view of a curved wedge distractor.

Referring to FIG. 22, a perspective view of a curved wedge distractor 700 is presented. The curved wedge distractor 700 has a gripping portion 702, an arcuate shaft 704, and a working end which is a wedge head 706, coupled to the distal end of the arcuate shaft 704. The arcuate shaft 704 follows an arcuate shaft pathway similar to the arcuate shaft pathway 512 of the curved curette 500. At the proximate end of the gripping portion 702 is an impaction surface 708. During a distraction procedure, a mallet or other striking instrument may be used to apply force to the curved wedge distractor 700, and the impaction surface 708 is an area reinforced to withstand the blows and translate the force distally toward the wedge head 706. The wedge head 706 has a wedge-shaped peaked portion 710, and a wider rectangular block portion 712. As force is applied to the wedge distractor 700, the smaller peaked portion 710 first enters the interbody space, gradually wedging it apart; the block portion 712 that follows maintains the distraction. A stabilization feature 714 is a wide portion of the arcuate shaft 704 which is configured to fit just inside the arcuate cannula 18 (not shown). The stabilization feature 714 allows the wedge head 706 to enter the interbody space on a precisely defined path, and stabilizes the position of the entire distractor 700 as force is applied to the impaction surface 708.

It is appreciated that the wedge head 706 may be configured in a variety of ways. For example, the wedge distractor 750 in FIG. 17 has a wedge head which has no block portion. Alternatively, the wedge head may vary in the angle of the wedge, width or length of the wedge portion, width, height or length of the block portion, ratio of wedge portion to block portion, and number of sides, among other dimensions. A series of wedge distractors with wedge heads of graduated sizes may be used to sequentially distract the interbody space. The height of a wedge distractor head chosen for a procedure may match the height of an implant used in the same procedure.

Figure 23:
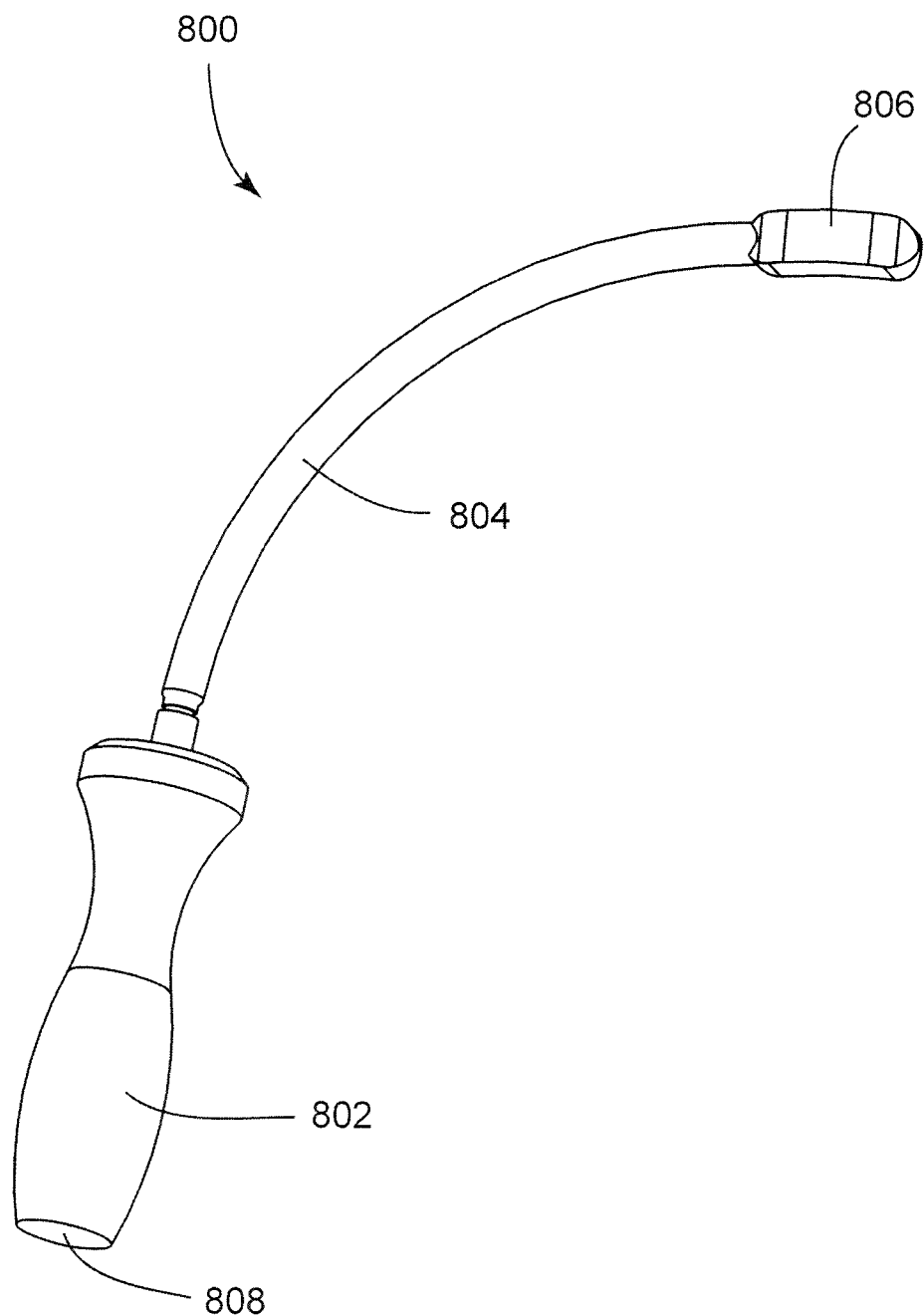
FIG. 23 is a perspective view of a curved trial implant instrument.

Referring to FIG. 23, a perspective view of a trial implant instrument 800 is shown. The trial implant instrument 800 has a gripping portion 802 and a working portion comprising an arcuate shaft 804 and a working end. The arcuate shaft 804 follows an arcuate shaft pathway similar to the arcuate shaft pathway 512 of the curved curette 500. At the proximal end of the gripping portion 802 is an impaction surface 808, which is reinforced to withstand force from a mallet or other striking instrument. At the distal terminus of the arcuate shaft 804 is the working end, which is a trial implant 806. The trial implant 806 is curved along the same trajectory as the arcuate shaft 804. The trial implant 806 may be permanently coupled to the distal end of the shaft 804, or may be releasably attached, allowing for substitution of alternate trial implants. It is appreciated that a variety of trial implants (or, if the trial implant 806 is not detachable from the arcuate shaft 804, a variety of trial implant instruments) that vary in function, shape and/or size may be provided to allow practitioners to insert and remove several trial implants in order to determine and select the properly configured implant for final implantation.

Figure 24:
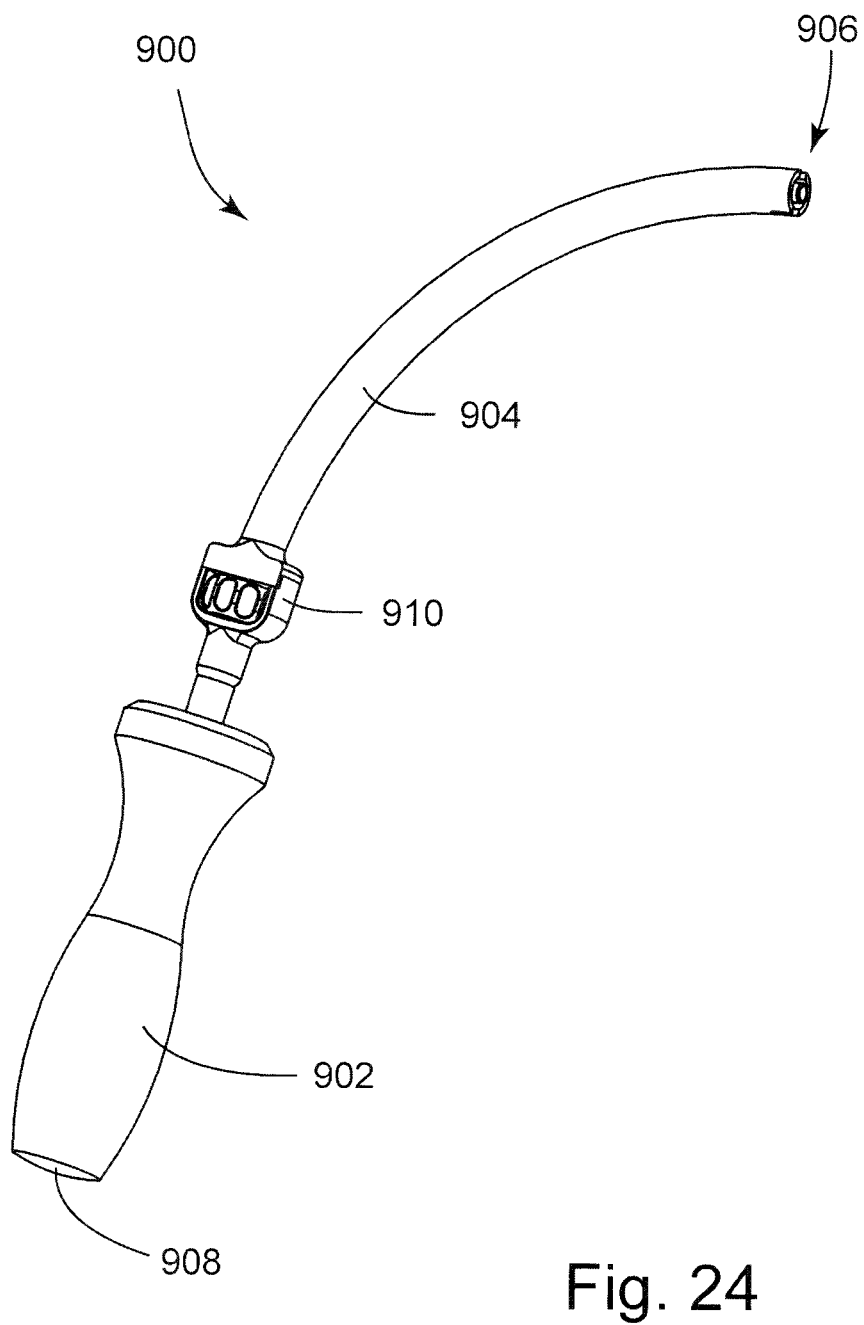
FIG. 24 is a perspective view of a curved implant inserter.

Referring to FIG. 24, a perspective view of an implant inserter 900 is shown. The implant inserter 900 has a gripping portion 902 and an arcuate shaft 904. The arcuate shaft 904 follows an arcuate shaft pathway similar to the arcuate shaft pathway 512 of the curved curette 500. Coupled to the distal end of the arcuate shaft 904 is a working end which is an implant connector 906. An implant retaining mechanism 910 is located on the arcuate shaft 904; on other embodiments of the invention it may be located on the gripping portion 902. The implant retaining mechanism 910 is linked to the implant connector 906 through the arcuate shaft 904, and allows for controlled retention and release of a spinal implant such as the interbody implant 300 of FIGS. 15A and 15B. The implant retaining mechanism 910 may be sized to fit within the arcuate envelope defined by an arcuate cannula such as the cannula 18. An impaction surface 908, which is reinforced to withstand force from a mallet or other striking instrument, may be located at the proximal end of the gripping portion 902.

Figure 25:
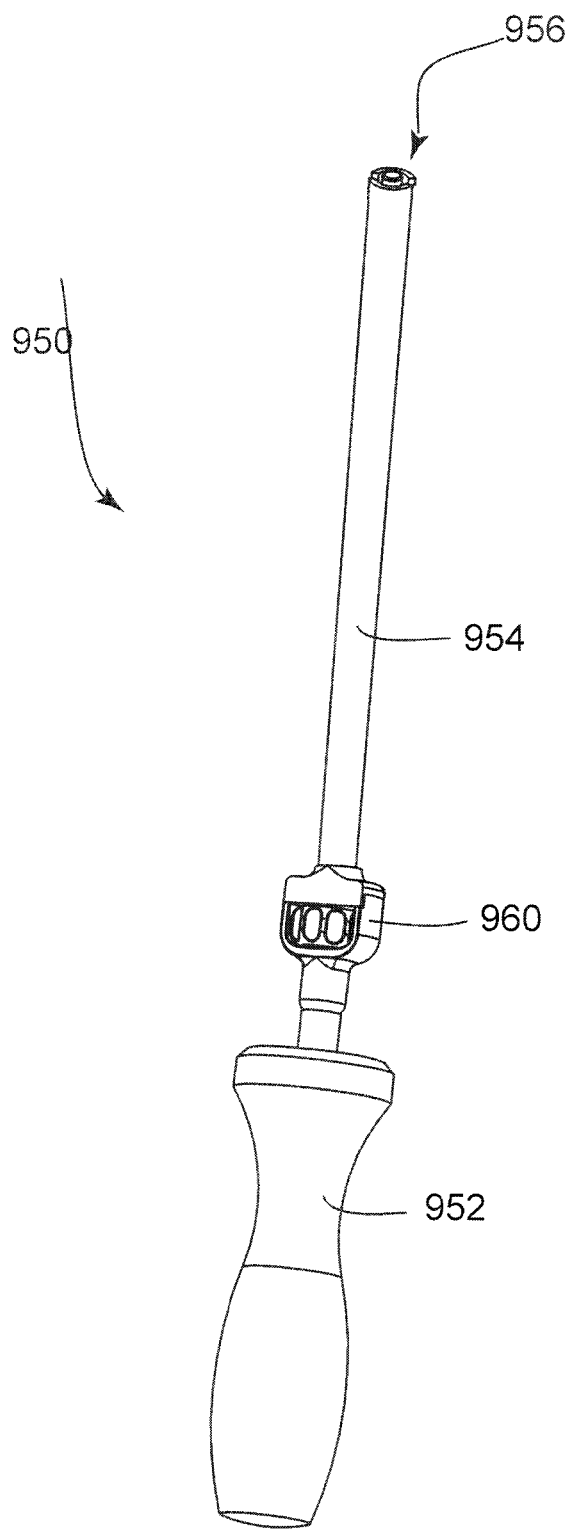
FIG. 25 is a perspective view of an implant inserter with a flexible shaft.

A flexible implant inserter with a flexible shaft is shown in FIG. 25. Flexible implant inserter 950 has a gripping portion 952 and a flexible shaft 954. The flexible shaft 954 may have a straight position as depicted in FIG. 25, and may flex to attain a curved position. Coupled to the distal end of the flexible shaft 954 is a working end which is an implant connector 956. Similar to the implant inserter 900, flexible implant inserter 950 has an implant retaining mechanism 960 which is linked to the implant connector 906. A spinal implant such as the interbody implant 300 of FIGS. 15A and 15B may be connected to the implant connector 956; then the implant 300 and the flexible shaft 954 may be inserted through the cannula 18 of FIG. 16. As the flexible shaft 954 moves through the cannula 18, it can flex to match the curvature of the cannula 18, and thus, the curvature of the arcuate envelope pathway 136. After the implant 300 is positioned in the interbody space, it is released via actuation of the implant retaining mechanism 910, and the flexible implant inserter 950 is withdrawn from the cannula 18.

Figure 26:
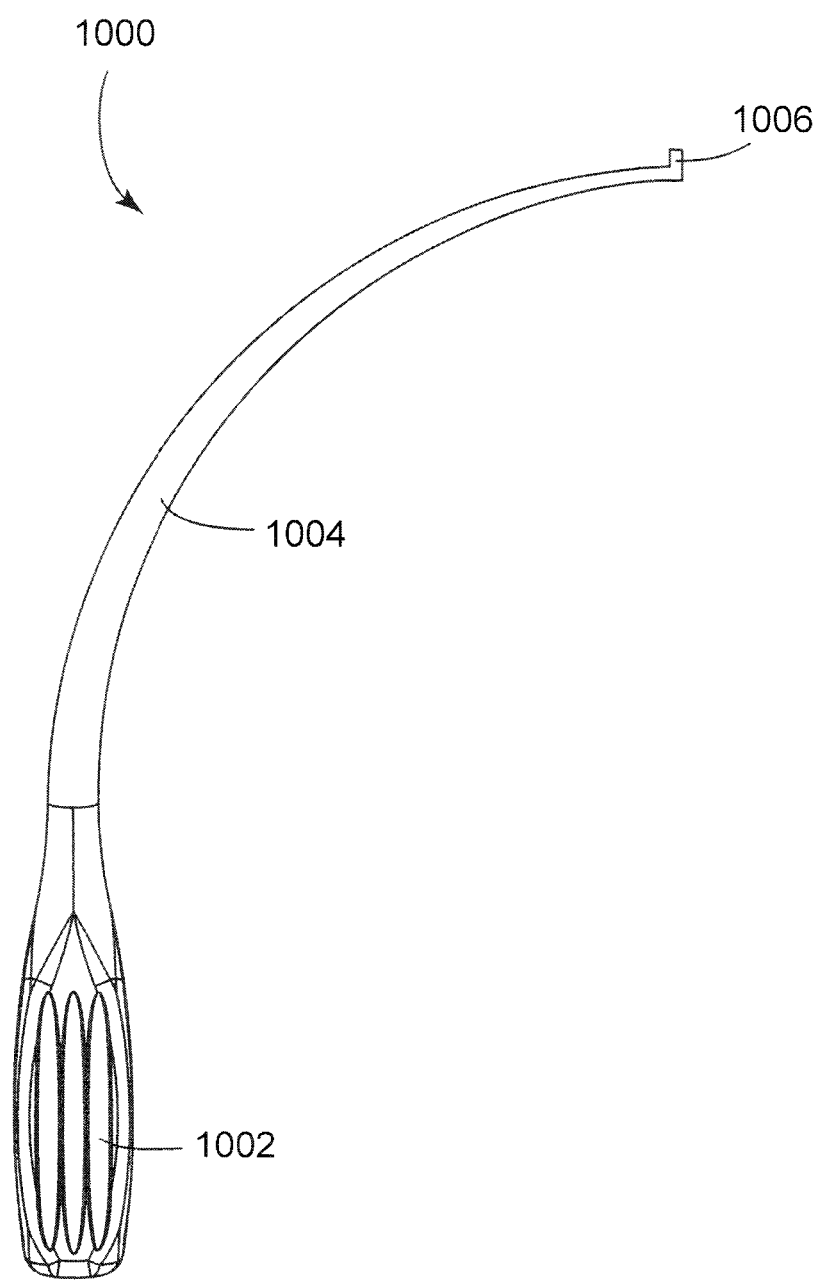
FIG. 26 is a perspective view of a curved probe.

Referring to FIG. 26, a perspective view of a curved probe 1000 is shown. The curved probe 1000 has a gripping portion 1002 and an arcuate shaft 1004 which follows an arcuate shaft pathway similar to the arcuate shaft pathway 512 of the curved curette 500. Extending perpendicularly from the distal end of the arcuate shaft 1004 is a working end which is a probe tip 1006. The arcuate shaft 1004 and probe tip 1006 may be inserted through the arcuate cannula 18 (not shown) to probe and test the spinal surgical site during a spinal surgical procedure to locate anatomy or carry out other functions. Shown in FIG. 26 is a probe tip 1006 which extends anteriorly when used with the arcuate cannula assembly 10; however the probe tip 1006 may be configured to extend posteriorly, laterally or in any direction from the distal end of the arcuate shaft 1004.

Figure 27:
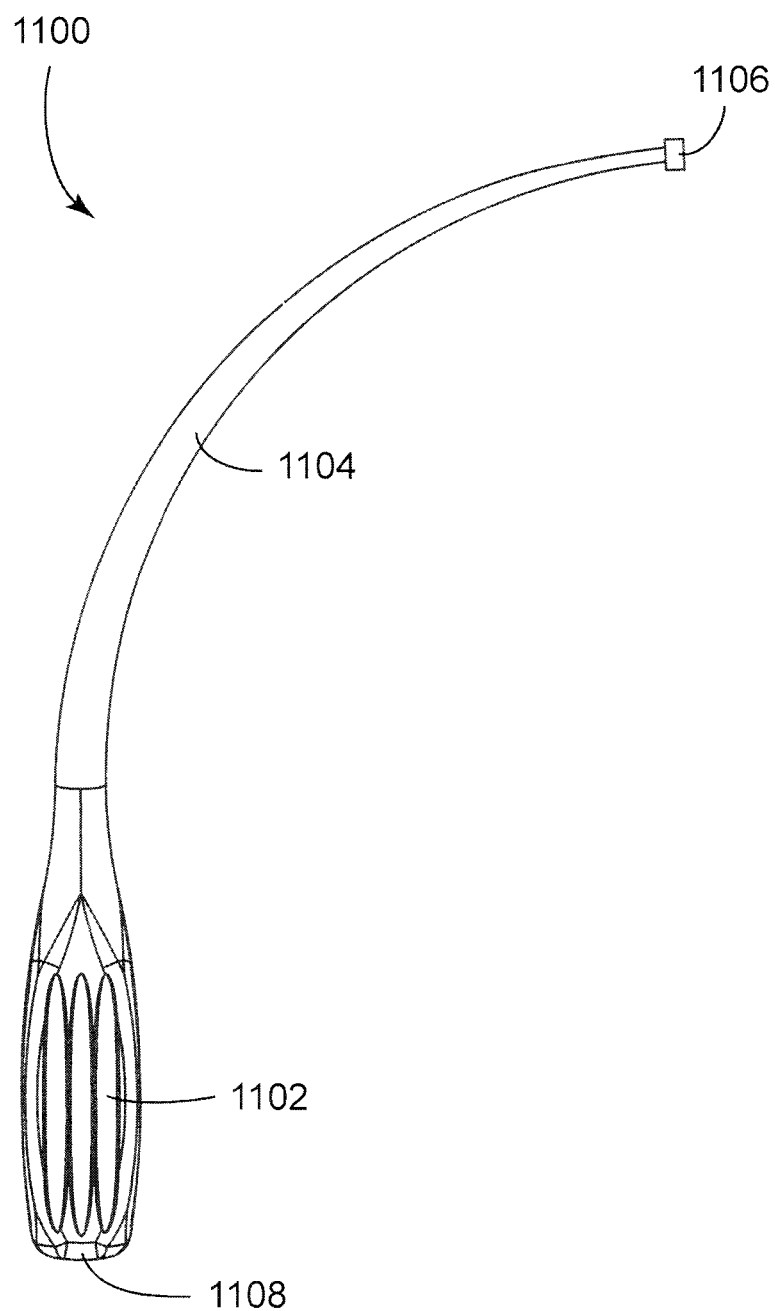
FIG. 27 is a perspective view of a curved tamp.

Referring to FIG. 27, a perspective view of a curved tamp 1100 is shown. The curved tamp 1100 has a gripping portion 1102 and an arcuate shaft 1104 which may follow an arcuate shaft pathway similar to the arcuate shaft pathway 512 of the curved curette 500. Coupled to the distal end of the arcuate shaft 1104 is a working end which is a tamp head 1106. After placement of the interbody implant 300 or other implant with the implant inserter 900, the curved tamp 1100 may be used through the cannula 18 to fine tune the placement of the implant. A reinforced impaction surface 1108 may be located on the proximal end of the gripping portion 1102.

Each of the instruments set forth above and depicted in FIGS. 17-27 is configured to be inserted through the arcuate cannula 18 in the manner depicted in FIG. 17. Except for the flexible implant inserter 950, the shaft of each instrument may be formed of a rigid material and in a rigid arcuate configuration. Alternatively the shaft of each instrument may be formed of a compliant material which can flex to attain an arcuate configuration and pass through the arcuate envelope defined by the arcuate cannula, similar to the flexible implant inserter 950. Such instruments formed with flexible shafts may also be used to reach through cannulas which are curved, but do not have a fixed radius of curvature.

The gripping portion of each instrument may be coupled to the shaft in the orientation depicted for each instrument in FIGS. 17-27. Alternatively, the gripping portion of any instrument may be coupled to the shaft so that the gripping portion is at an angle relative to the shaft. More precisely, the gripping portion may be oriented at an angle perpendicular to the proximal end of the shaft. In another embodiment, the gripping portion may be oriented such that a longitudinal axis of the gripping portion is parallel to a longitudinal axis of the working end. In such an orientation, a motion at the gripping portion of the instrument may translate to an equivalent motion at the working end, giving enhanced tactile control to the user of the instrument.

To perform a particular spinal procedure, one or more of the curved instruments set forth above may be inserted through the arcuate cannula to access the spinal surgical site. For example, to perform an interbody device implantation between two vertebrae, a first instrument such as the curved curette 500, curved rasp 600 or curved rongeur 400 is inserted into the arcuate cannula and its working end employed to prepare the intervertebral space and vertebral endplates. The instrument is removed and a second preparatory instrument, or more, from the same group may be inserted and used if necessary. When preparation of the intervertebral space and endplates is complete, a curved trial implant instrument 800 may be used to insert variously sized trial implants through the cannula to determine the correct size for an interbody implant. Finally, the interbody implant 300 is inserted through the cannula using the curved implant inserter 900, released and implanted in the interbody space. The curved tamp 1100 may then be used to adjust the positioning of the implanted implant 300.

Figure 28:
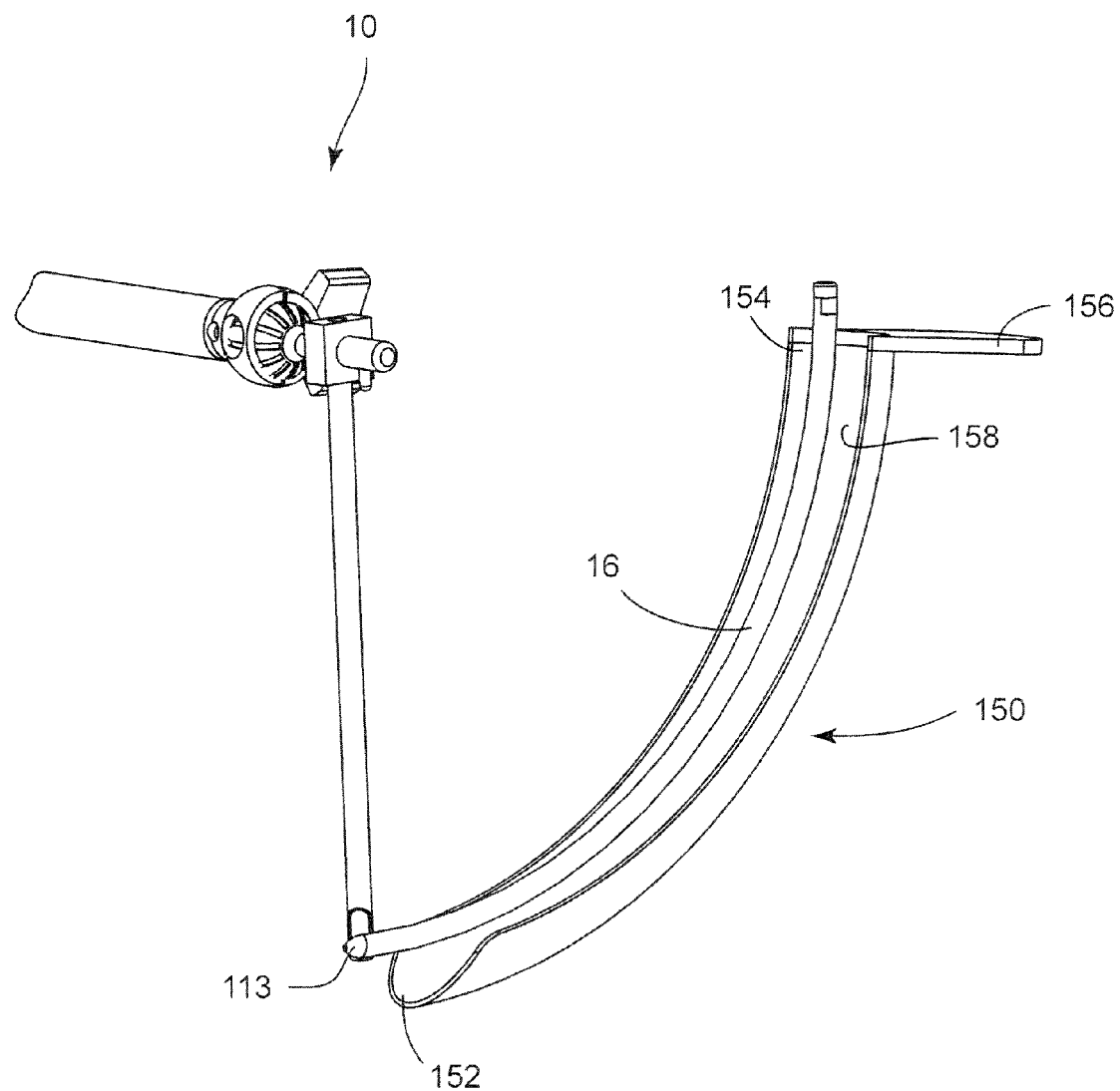
FIG. 28 is a perspective view of an arcuate cannula assembly and a peritoneal retractor.

An alternative embodiment of the invention is shown in FIG. 28. A peritoneal retractor 150 may be used with the arcuate cannula assembly 10 to retract and protect the tissues surrounding the path of the associated cannula 18 or dilator. The peritoneal retractor 150 has a curved half-pipe configuration, with a rounded distal end 152 and a proximal end 154. A flat lip 156 extends perpendicularly from the proximal end 154, and can be used to grip and guide the peritoneal retractor 150. The peritoneal retractor 150 is curved longitudinally to match the curve of the guide member 16, the cannula 18, and any intermediate cannulas used to facilitate dilation of the opening through the tissues. A curved guiding surface 158 extends from the proximal end 154 to the distal end 152, to provide guidance for the guide member 16 and cannulas as they are introduced.

The peritoneal retractor 150 is introduced into the patient after a targeting post is introduced as set forth previously. After the surgeon has marked the incision location and made the incision, the surgeon may insert a finger into the incision to locate and palpate the soft tissues and fascia. Next, the peritoneal retractor 150 may be gradually inserted along the path of the finger to both shield and retain the tissues. The retractor 150 may be inserted until the rounded distal end 152 comes in contact with the psoas muscle. The guide member 16 is then advanced antero-medially along the arcuate path of the curved guiding surface 158 until the insertion tip 113 is at the lateral margin of the targeted disc, at a target location. The peritoneal retractor 150 remains in place as the series of graduated cannulas 15, 17, 18 of FIG. 11 are introduced over the guide member 16 as set forth previously; the retractor 150 may make insertion of the cannulas 15, 17, 18 easier by preventing the surrounding tissues from enveloping the guide member. After completion of the surgical procedure, the largest cannula 18 is removed, and finally the retractor 150 is removed after removal of the cannula 18.

Figure 29:
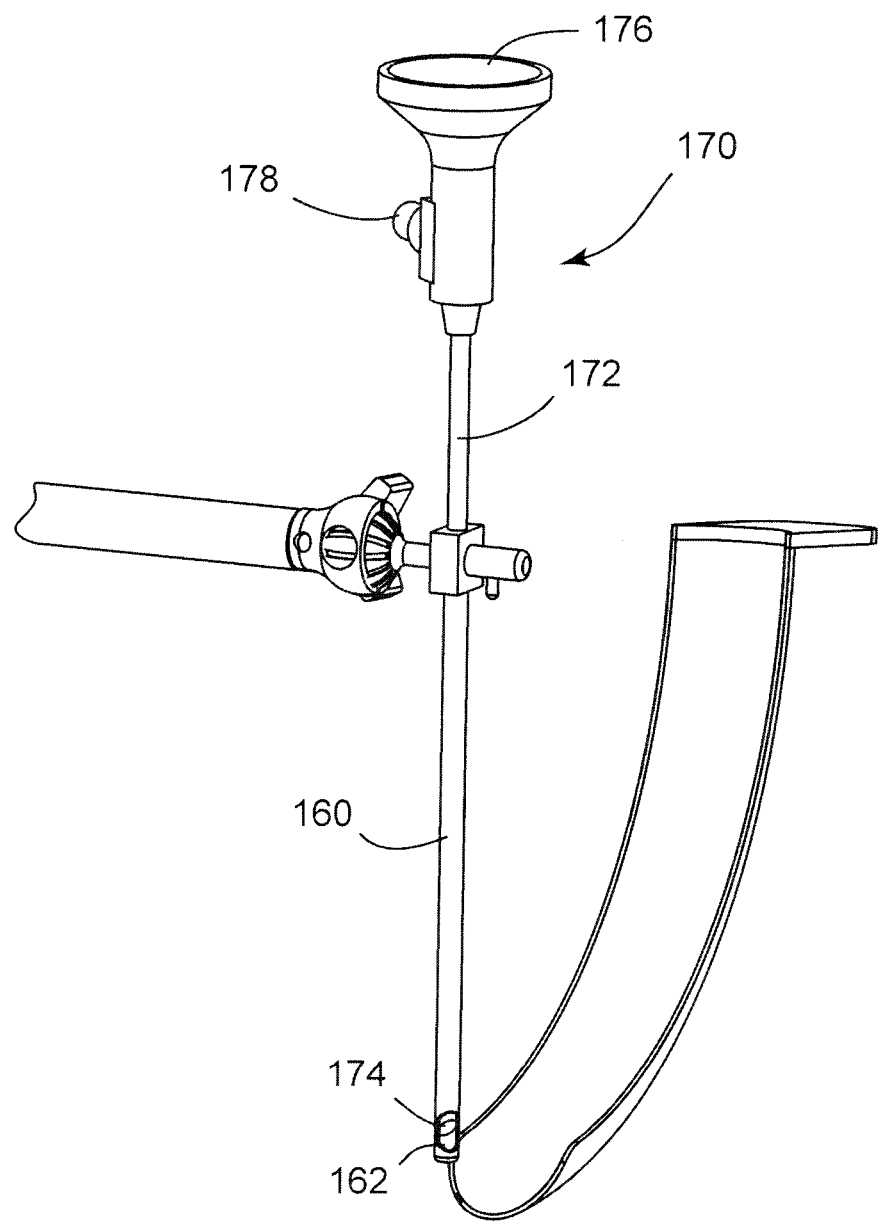
FIG. 29 is a perspective view of an arcuate cannula assembly and an endoscope.

Another embodiment of the invention includes a visualization component, such as an endoscope. Referring to FIG. 29, an endoscope 170 is used with the arcuate cannula assembly 10. The endoscope has a tube 172 which terminates distally with an aperture 174, and has a viewing portal 176 at a proximal end. A video connection 178 is located near the viewing portal 176. The endoscope is deployed by inserting the tube 172 through a hollow targeting post 160 with an opening 162 at its distal end. By looking through the viewing portal 176 or using the video connection 178 to a separate display screen, the surgeon can view the surgical procedure at the targeted location. A light source including fiber optics may be used to provide light to the location. Alternatively, the endoscope may include a flexible tube and be inserted through the arcuate cannula, or the targeting post.

The arcuate postero-lateral approach described above may have many advantages for spinal procedures, particularly procedures involving anterior vertebral column elements. This approach may be used to insert motion preservation devices, such as total disc replacements. By accessing the disc space via an arcuate postero-lateral approach, the surgeon is able to spare the anterior longitudinal ligament as well as avoid complications with the great vessels. This approach also provides for revision options with virtually the same instrumentation and implant designs by accessing the disc space from the opposite lateral side as the first surgery. This approach also allows for total disc replacement (TDR) endplate retention features which are more desirable than anterior approach TDR features, such as endplate keels or teeth which are oriented in the frontal plane to resist the high shear loads seen in the lumber spine lordotic region.

This approach may also be used for various intervertebral disc treatment or resection procedures such as annulotomy, nucleotomy, discectomy, annulus replacement, nucleus replacement, and decompression due to a bulging or extruded disc. During an annulotomy, the surgeon may provide an access portal in the manner described previously, and open and/or remove a portion or all of the disc annulus. During a nucleotomy, the surgeon may provide an access portal in the manner described previously, and open and/or resect a portion of the intervertebral disc nucleus. During a discectomy, the surgeon may remove a portion or the entire intervertebral disc through the access portal in order to accomplish decompression of the nerve roots, dura, or spinal cord. This procedure may be done as a conservative therapy to relieve patient symptoms or pain, or it may be done in preparation for total disc replacement or fusion.

For annulus repair or replacement, the arcuate postero-lateral approach may facilitate a larger needle and avoidance of complicated vascular structure and may allow a pathway for a prosthetic annulus to be placed or formed in the intervertebral space. Using a bilateral arcuate approach such as that depicted in FIG. 14 could further facilitate the creation of bounding elements, such as a shield, guard, mold, or equivalent such that the annulus may be repaired, formed, inserted, created, or augmented. Similar benefits are realized for a nucleus replacement procedure where all or a portion of the intervertebral nucleus is repaired or resected and replaced, created or augmented via various techniques. A prosthetic nucleus may be delivered via a passageway that is larger than that afforded by a transpedicular approach, and less complicated and less risky than an anterior approach, by using the arcuate postero-lateral approach described above. Various intervertebral disc treatment methods have been postulated, such as using electrosurgical therapies. It is readily apparent to one of skill in the art how conducting these therapies via an arcuate postero-lateral approach may benefit the surgeon as well as improve clinical outcomes.

The arcuate postero-lateral approach may also be utilized for additional vertebral body motion segment stabilization procedures such as interbody device insertion, lateral plating, anterior plating, lateral or anterior plating with dynamic stabilization or compression elements, deformity correction, and/or graft compression devices or procedures. The arcuate postero-lateral access portal such as that depicted in FIG. 15A may facilitate interbody fusion procedures by allowing a single surgical exposure or patient positioning to insert all required stabilization elements such as an interbody fusion device similar to that depicted in FIG. 15B, or posterior stabilization hardware such as pedicle screws, rods, hooks, and facet screws, among others. By approaching the intervertebral disc space with a tangential or almost straight medial-lateral trajectory right next to the vertebral body, the interbody device may more fully occupy the intervertebral space. This may result in a multitude of advantages such a leveraging the higher strength cortical regions on the vertebral body endplates, allowing more cross-sectional surface area or a larger footprint for improved stability, allowing more bone graft surface are to encourage better osteointegration, bony fusion, and 360° fusion. The interbody device may also comprise a lordotic angle which does not require over-distraction such as is the case with transforaminal lumbar interbody fusion (TLIF) and posterior lumbar interbody fusion (PLIF) procedures.

The arcuate postero-lateral approach may also be used for lateral plating procedures, in which the implanted plates may comprise fixed, dynamic, or compressive elements. This approach again allows a single patient positioning to conduct lateral plating as well as posterior stabilization hardware such as screws, hooks and rods. These plates may be used for local deformity correction or prevention procedures to treat local scoliosis, kyphosis, hyper-lordosis, or spondylolisthesis. Additionally, the arcuate postero-lateral approach may allow for novel graft compression devices or procedures that enable the surgeon to apply improved local compressive forces between vertebral bodies or an interbody device. Benefits of improved local compressive forces include improved bone graft incorporation, fusion, interbody device stability, as well as a potentially reduced risk of interbody device expulsion that is often the result of over-compressing the disc space and applying unintended moments via traditional pedicle screws and rods. Such graft compression devices include lateral plates with compression features, vertebral body staples which cooperate with the superior and inferior vertebral bodies to apply compression, and integrated interbody device with arms that cooperate with the vertebral bodies to apply compression via screws, tapered surfaces, or the like.

Various central canal or foraminal decompression procedures may be performed with the arcuate postero-lateral approach described previously. Decompression procedures are conducted to resect soft or hard tissues that may be impinging on neural elements such as the exiting nerve roots, dura, or spinal cord, resulting in various pathologies such as radiculopathy, myelopathy, pain, tingling, numbness, and loss of motor or sensory control. For example, anterior central canal decompression required due to a diseased intervertebral disc is often a difficult procedure. By using the disclosed arcuate postero-lateral approach, this decompression procedure allows for improved patient positioning, access, and patient outcomes. Foraminal decompression procedures via an arcuate postero-lateral approach may also allow the surgeon an improved trajectory and passageway to decompress the foramen.

Procedures involving the vertebral body, such as vertebral body biopsy, vertebral body height restoration, and vertebroplasty may successfully utilize the arcuate postero-lateral approach. Often patients who are experiencing symptoms associated with vertebral body disease, collapse, or fracture will undergo a biopsy of the vertebral body to assess the condition of the structure. Osteoporotic patients, especially female geriatric patients, may experience vertebral body collapse or fracture. This is an extremely painful and debilitating condition which may be addressed via vertebroplasty through the disclosed arcuate postero-lateral approach. Often, vertebroplasty, kyphoplasty or arcuplasty procedures are conducted via a transpedicular approach, to inject a hardenable compound such as PMMA cement into the vertebral body to create an internal cast-like structure to stabilize the bony fragments or fractures. The arcuate postero-lateral approach has numerous advantages for such a procedure. It may allow for a larger access needle than a transpedicular approach and accordingly reduces pressure requirements for the viscous hardenable compounds. In addition, it will likely result in less post-operative pain due to not violating the pedicle, and it allows for a more preferable trajectory of the access needle. Vertebroplasties conducted via a transpedicular approach often require a bilateral approach for sufficient vertebral body stabilization. By using the trajectory of the arcuate postero-lateral approach, the surgeon or radiologist may use a single needle and single approach for a complete fill, because the access needle can be advanced to the distal portions and gradually retracted during injection to accomplish a complete fill.

Vertebral body height restoration procedures have recently been disclosed in the art to address collapsed vertebral bodies. The arcuate postero-lateral approach may facilitate such vertebral height restoration procedures by removing the size limitation imposed by the transpedicular approach. Additionally, the ability to access the lateral margins of the vertebral body may be beneficial in insertion of an implant to restore vertebral height and fix it in place via a hardenable compound, or conduct an internal vertebral body distraction and secure the vertebral body via a hardenable compound.

The present invention may be embodied in other specific forms without departing from its spirit or essential characteristics. For example, above are described various alternative examples of systems for accessing intervertebral space. It is appreciated that various features of the above-described examples can be mixed and matched to form a variety of other alternatives. It is also appreciated that this system should not be limited creating access to the intervertebral space. This arcuate access system may be used to obtain access to any portion of the spine. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A system, comprising: a curved penetrating guide member with a proximal end and a distal end; a curved cannula having a proximal end and a distal end and shaped to extend along a curved pathway; wherein the curved penetrating guide member and the curved cannula are not coupled and spaced apart from one another in a first configuration, wherein the curved penetrating guide member and the curved cannula are configured such that the distal end of the curved cannula can be inserted over the proximal end of the curved penetrating guide member and advanced toward the distal end of the curved penetrating guide member in a second configuration; and a spinal orthopedic instrument, comprising: a gripping portion; and a working portion, comprising: an arcuate shaft having a proximal end coupled to the gripping portion, and a distal end; and a working end coupled to the distal end; wherein the arcuate shaft extends along an arcuate shaft pathway having a minimum radius of about 2 inches; wherein the spinal orthopedic instrument is selected from the group consisting of a rongeur, a curette, a rasp, a wedge distractor, a trial implant, an interbody implant inserter, a probe, and a tamp.

2. The system of claim 1, further comprising an interbody implant, wherein the spinal orthopedic instrument comprises an interbody implant inserter, wherein the distal end is configured to releasably retain the interbody implant to facilitate implantation of the interbody implant within an interbody space between first and second vertebrae of a spine.

3. The system of claim 1, further comprising an implant, wherein the working end comprises a trial implant insertable into a spinal surgical site to facilitate determination of whether the implant is properly implantable in the spinal surgical site.

4. The system of claim 1, wherein the spinal orthopedic instrument comprises an endplate preparation tool selected from the group consisting of a curette, a rongeur, and a rasp.

5. A system, comprising: a curved penetrating guide member with a proximal end and a distal end; a curved cannula having a proximal end and a distal end and shaped to extend along a curved pathway; wherein the curved penetrating guide member and the curved cannula are not coupled to one another and spaced apart from one another in a first configuration, wherein the curved penetrating guide member and the curved cannula are configured such that the distal end of the curved cannula can be inserted over the proximal end of the curved penetrating guide member and advanced toward the distal end of the curved penetrating guide member in a second configuration; an implant shaped to pass through the cannula; and a spinal orthopedic instrument, comprising: a gripping portion; and a working portion coupled to the gripping portion, the working portion having a shaft and a working end; wherein the working portion is shaped to pass through the cannula; wherein the implant is selected from the group consisting of an interbody implant, a nucleus replacement, an annulus replacement, a staple, a lateral plate, a lateral plate-interbody implant combined device, an artificial disc, a therapeutic-containing implant, a vertebral body screw, a vertebral body anchor, and a facet replacement.

6. The system of claim 5, wherein the spinal orthopedic instrument is selected from the group consisting of a rongeur, a curette, a rasp, a wedge distractor, a trial implant, an implant inserter, a probe, and a tamp.

7. The system of claim 5, wherein the implant comprises an interbody implant configured to be implanted within an interbody space between first and second vertebrae of a spine.

8. The system of claim 5, wherein the shaft is rigid and possesses a curvature that corresponds to the curved pathway.

9. The system of claim 5, wherein the shaft is sufficiently flexible to enable the shaft to bend with a curvature that corresponds to the curved pathway.

* * * * *